US012569464B2

(12) United States Patent
Crew et al.

(10) Patent No.: US 12,569,464 B2
(45) Date of Patent: Mar. 10, 2026

(54) PROTEIN-PROTEIN INTERACTION INDUCING TECHNOLOGY

(71) Applicant: Arvinas Operations, Inc., New Haven, CT (US)

(72) Inventors: Andrew P. Crew, Chester, CT (US); Hanqing Dong, Madison, CT (US); Brian Hamman, Orange, CT (US); Taavi K. Neklesa, Orange, CT (US); Yimin Qian, Plainsboro, NJ (US); Jing Wang, Milford, CT (US); Kurt Zimmermann, Durham, CT (US)

(73) Assignee: Arvinas Operations, Inc., New Haven, CT (US)

( * ) Notice: Subject to any disclaimer, the term of this patent is extended or adjusted under 35 U.S.C. 154(b) by 1237 days.

(21) Appl. No.: 17/356,751

(22) Filed: Jun. 24, 2021

(65) Prior Publication Data

US 2021/0315856 A1 Oct. 14, 2021

Related U.S. Application Data

(63) Continuation of application No. 15/477,966, filed on Apr. 3, 2017, now abandoned.

(60) Provisional application No. 62/318,630, filed on Apr. 5, 2016.

(51) Int. Cl.

| | |
|---|---|
| ***A61K 47/55*** | (2017.01) |
| ***A61K 31/277*** | (2006.01) |
| ***A61K 31/4166*** | (2006.01) |
| ***A61K 31/551*** | (2006.01) |
| ***A61K 38/05*** | (2006.01) |
| ***G01N 33/68*** | (2006.01) |
| ***G16B 15/00*** | (2019.01) |
| ***G16B 15/30*** | (2019.01) |
| ***G16B 20/00*** | (2019.01) |
| ***G16B 20/30*** | (2019.01) |
| ***G16C 20/50*** | (2019.01) |

(52) U.S. Cl.

CPC ........ *A61K 31/277* (2013.01); *A61K 31/4166* (2013.01); *A61K 31/551* (2013.01); *A61K 38/05* (2013.01); *A61K 47/55* (2017.08); *G01N 33/6845* (2013.01); *G16B 15/30* (2019.02); *G16B 20/00* (2019.02); *G16B 20/30* (2019.02); *G16C 20/50* (2019.02); *G16B 15/00* (2019.02)

(58) Field of Classification Search

None

See application file for complete search history.

(56) References Cited

U.S. PATENT DOCUMENTS

| | | | |
|---|---|---|---|
| 4,522,811 | A | 6/1985 | Eppstein |
| 6,306,663 | B1 | 10/2001 | Kenten et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Sakamoto et al. |
| 9,500,653 | B2 | 11/2016 | Crews et al. |
| 9,632,089 | B2 | 4/2017 | Crews et al. |
| 2007/0254933 | A1 | 11/2007 | Jung et al. |
| 2008/0051432 | A1 | 2/2008 | Zhang |
| 2008/0214501 | A1 | 9/2008 | Pan et al. |
| 2009/0035362 | A1 | 2/2009 | Shih et al. |
| 2010/0048517 | A1 | 2/2010 | Hu et al. |
| 2010/0286127 | A1 | 11/2010 | Miyoshi et al. |
| 2011/0172981 | A1 | 7/2011 | Al-Hashimi et al. |
| 2012/0270800 | A1 | 10/2012 | Verdine et al. |
| 2014/0193334 | A1 | 7/2014 | Bierbach |
| 2014/0256700 | A1 | 9/2014 | Poss |
| 2014/0296243 | A1 | 10/2014 | Albrecht et al. |
| 2014/0302523 | A1 | 10/2014 | Crews et al. |
| 2014/0356322 | A1 | 12/2014 | Crews et al. |
| 2014/0371206 | A1 | 12/2014 | Albrecht et al. |
| 2015/0119435 | A1 | 4/2015 | Crews et al. |

(Continued)

FOREIGN PATENT DOCUMENTS

| | | | |
|---|---|---|---|
| CN | 1844118 | A | 10/2006 |
| CN | 103688176 | A | 3/2014 |

(Continued)

OTHER PUBLICATIONS

Ahn, et al., "HIF-lalpha peptide derivatives with modifications at the hydroxyproline residue as activators of HIF-lalpha", Bioorg Med Chem Lett. 19(15), 2009, 4403-4405.

(Continued)

*Primary Examiner* — Olivia M. Wise

*Assistant Examiner* — Jonathan Edward Hayes

(74) *Attorney, Agent, or Firm* — McCarter & English, LLP; Michael J. DeGrazia; James M. Alburger

(57) ABSTRACT

The present disclosure is based on the surprising and unexpected discovery that a ligand molecule with certain characteristics is able to bind to two protein molecules simultaneously and recruit them to form a transient or stable protein-protein interaction complex. The protein-protein interaction and other cross-domain interactions gained in this process contribute additional stabilization energy to the complex beyond the combination of the binary binding energies, and therefore, largely increase the binding potency of the ligand. Accordingly, the present disclosure provides a Protein-Protein Interaction Inducing Technology (PPIIT), which includes a method to design and identify the tripartite or bifunctional compounds and use such compounds to induce protein-protein interactions in various contexts. The present disclosure also provides a composition for the purpose of inducing protein-protein interactions.

13 Claims, 7 Drawing Sheets

(56) References Cited

U.S. PATENT DOCUMENTS

| | | | |
|---|---|---|---|
| 2015/0148342 | A1 | 5/2015 | Combs et al. |
| 2015/0291562 | A1 | 10/2015 | Crew et al. |
| 2015/0344473 | A1 | 12/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Arvinas |
| 2016/0136230 | A1 | 5/2016 | Campos et al. |
| 2016/0176864 | A1 | 6/2016 | Norris et al. |
| 2016/0214972 | A1 | 7/2016 | Jin et al. |
| 2016/0243247 | A1 | 8/2016 | Bradner et al. |
| 2016/0272639 | A1 | 9/2016 | Crew et al. |
| 2016/0368911 | A1 | 12/2016 | Campos et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |
| 2018/0015087 | A1 | 1/2018 | Liu et al. |
| 2018/0072711 | A1 | 3/2018 | Crew et al. |
| 2018/0099940 | A1 | 4/2018 | Crew et al. |
| 2018/0125821 | A1 | 5/2018 | Crew et al. |
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |

FOREIGN PATENT DOCUMENTS

| | | | |
|---|---|---|---|
| EP | 2985285 | | 2/2016 |
| JP | A 2004-525889 | | 8/2004 |
| JP | A 2010-502627 | | 1/2010 |
| RU | 2008112221 | A | 10/2009 |
| RU | 2448101 | C2 | 4/2012 |
| RU | 2011121567 | A | 10/2012 |
| RU | 2012138709 | A | 3/2014 |
| WO | WO 1998/003502 | | 1/1998 |
| WO | WO 2000/066119 | | 11/2000 |
| WO | WO 2002/000617 | | 1/2002 |
| WO | WO 2002/066512 | | 8/2002 |
| WO | WO 2002/100845 | | 12/2002 |
| WO | WO 2006/113942 | | 10/2006 |
| WO | WO 2007/106670 | | 9/2007 |
| WO | WO 2008/011392 | | 1/2008 |
| WO | WO 2009/015254 | | 1/2009 |
| WO | WO 2010/141805 | | 12/2010 |
| WO | WO 2011/008260 | | 1/2011 |
| WO | WO 2011/143660 | | 11/2011 |
| WO | WO 2011/143669 | | 11/2011 |
| WO | WO 2012/003281 | | 1/2012 |
| WO | WO 2012/040527 | | 3/2012 |
| WO | WO 2012/078559 | | 6/2012 |
| WO | WO 2012/090104 | | 7/2012 |
| WO | WO 2013/106643 | | 7/2013 |
| WO | WO 2013/106646 | | 7/2013 |
| WO | WO 2013/170147 | | 11/2013 |
| WO | WO 2014/001356 | | 1/2014 |
| WO | WO 2014/108452 | | 7/2014 |
| WO | WO 2014/123418 | | 8/2014 |
| WO | WO 2014/128111 | | 8/2014 |
| WO | WO 2015/000868 | | 1/2015 |
| WO | WO 2015/011084 | | 1/2015 |
| WO | WO 2015/022332 | | 2/2015 |
| WO | WO 2015/015318 | | 5/2015 |
| WO | WO 2015/067770 | | 5/2015 |
| WO | WO 2015/074064 | | 5/2015 |
| WO | WO 2015/160845 | | 10/2015 |
| WO | WO 2015/195863 | | 12/2015 |
| WO | WO 2016/050821 | | 4/2016 |
| WO | WO 2016/069578 | | 5/2016 |
| WO | WO 2016/105518 | | 6/2016 |
| WO | WO 2016/118666 | | 7/2016 |
| WO | WO 2016/146985 | | 9/2016 |
| WO | WO 2016/169989 | | 10/2016 |
| WO | WO 2016/172134 | | 10/2016 |
| WO | WO 2016/197114 | | 12/2016 |
| WO | WO 2017/011590 | | 1/2017 |
| WO | WO 2017/030814 | | 2/2017 |
| WO | WO 2017/046036 | | 3/2017 |
| WO | WO 2017/079267 | | 5/2017 |
| WO | WO 2017/185036 | | 10/2017 |

OTHER PUBLICATIONS

Albrecht, B., et al., "Identification of a benzoisoxazoloazepine inhibitor (CPI-0610) of the bromodomain and extra-terminal (BETA) family as a candidate for human clinical trials", Journal Med. Chem. 59, 1330-1339 (2016).

Allan, GF, et al., "Therapeutic androgen receptor ligands", Nuclear Receptor Signaling, 2003, 1, e009 DOI:10.621.01009 9 1-4.

Asangani, I.A. et al., "Therapeutic Targeting of BET Bromodomain Proteins in Castration-Resistant Prostate Cancer", Nature, 2014, 510: 278-282.

Baratta, M.G. et al., "An in-tumor genetic screen reveals that the BET bromodomain protein, BRD4, is a potential therapeutic target in ovarian carcinonoma", PNAS, 112: 232-237 (2015).

Bargagna-Mohan, et al., "Use of Protacs as molecular probes of angiogenesis", Bioorg Med Chem Left. 15(11) 2005, 2724-2727.

Belkina, A.C. et al., "BET domain co-regulators in obesity, inflammation and cancer", Nat. Rev. Cancer, 12 (2012) 465-477.

Boi, M. et al., "The BET Bromodomain inhibitor OTX015 Affects pathogenetic Pathways in Preclinical B-cell Tumor Models and synergizes with Targeted Drugs", Clin. Cancer Res., (2015) 21(7):1628-1638.

Bondeson, et al., (2017) "Targeted Protein Degradation by Small Molecules." *Annu Rev Pharmacol Toxicol* 57:107-123.

Bondeson, et al., "Catalytic in vivo protein knockdown by small-molecule Protacs", National Chem Biol. 11(8) Aug. 2015, 611-617.

Bradbury, RH, et al., "Small-molecule androgen receptor downregulators as an approach to treatment of advanced prostate cancer", Bioorganic & Medicinal Chemistry Letters, 2011, 21: 5442-5445.

Braun, et al., "Quantitative analysis of bifunctional molecules", Biochemistry, vol. 43, pp. 2004, 5406-5407.

Buckley, et al., "HaloProtacs: use of small molecule Protacs to induce degradation of HaloTag fusion proteins", ACS Chem Biol. 10(8), 2015, 1831-1837.

Buckley, et al., "Small-molecule inhibitors of the interaction between the E3 ligase VHL and HIF1a", Angew Chem Int Ed Engl.51(46), Nov. 12, 2012, 11463-11467.

Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.

Burslem, et al., (2017) "Small-Molecule Modulation of Protein Homeostasis." *Chem Rev* 117(17):11269-11301.

Capitosti, S., et al., "Thalidomide analogues demonstrate dual inhibition of both angiogenesis and prostate cancer", Bioorganic & Medicinal Chemistry 12, (2004) 327-336.

Carmony, KC, et al., "Protac-Induced Proteolytic Targeting", Methods Mol. Biol., 2012, vol. 832, pp. 627-638.

CAS 155180-53-3 published 1994.

CAS 155255-73-5 published 1995.

CAS 186040-53-9 published 1997.

CAS 186798-71-0 published 1997.

CAS 186798-85-6 published 1997.

CAS 534612-78-7 published 2003.

CAS Registry No. 1004933-70-3, which entered STN on Feb. 21, 2008.

CAS Registry No. 1226974-40-8, indexed in the Registry file on STN CAS Online Jun. 4, 2010.

CAS Registry No. 871986-52-6 entered STN Jan. 16, 2006.

(56) References Cited

OTHER PUBLICATIONS

Ceribelli, M. et al., "Blockade of oncongenic IKB kinase activity in diffuse large B-cell lymphoma by bromodomain and extraterminal domain protein inhibitors", PNAS, 111 (2014) 11365-11370.
Chapuy, B. et al., "Discovery and characterization of super-enhancer-associated dependencies in diffuse large B cell lymphoma", Cancer Cell, 24 (2013) 777-790.
Chung, et al., "Discovery and Characterization of Small Molecule Inhibitors of the BET Family Bromodomains", J Med Chem. 54(11), Jun. 9, 2011, 3827-3838.
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crews, C. M., "Targeting the undruggable proteome: the small molecules of my dreams", *Chem Biol 17*, 551-555, doi:S1074-5521(10)00196-1 [pii] 10.1016/j.chembiol.2010.05.011 (2010).
Cromm, et al., (2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting Protacs", Chem Med Chem. 5(7), Jul. 5, 2010, 979-985.
Cyrus, K. et al., "Impact of Linker Length on the Activity of Protacs," Mol. Biosyst., 2011, vol. 7, No. 2, pp. 359-364.
Cyrus, K. et al., "Two-Headed Protac: An Effective New Tool for Targeted Protein Degradation," Chembiochem., 2010, vol. 11, pp. 1531-1534.
Dawson, et al., "Inhibition of BET recruitment to chromatin as an effective treatment for MLL-fusion leukemia", Nature 478, Oct. 2, 2011, 529-533.
Delmore, J.E. et al., "BET Bromodomain inhibition as a therapeutic strategy to target c-Myc", Cell, 146 (2011) 904-917.
Filippakopoulos, et al., "Selective inhibition of BET bromodomains", Nature 468, Dec. 23, 2010, 1067-1073.
Fischer, et al., "Structure of the DDB1-DRBN E3 Ubiquitin ligase in complex with thalidomide", Nature, vol. 000, pp. 1-5 (2014).
Fisher, et al., "Structure of the DDB1-CRBN E3 ubiquitin ligase in complex with thalidomide", Nature, 2014, 00 Month, vol. 000, pp. 1-16.
French, C.A. et al., "BRD-NUT oncoproteins: a family of closely related nuclear proteins that block epithelial differentiation and maintain the growth of carcinoma cells", Oncogene, 27 (2008) 2237-2242.
Gadd, M.S., et al., "Structural basis of Protac cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Guo C., et al., "Design of oxobenzimidazoles and oxindoles as novel androgen receptor antagonists", Bioorganic & Medicinal Chemistry Letters, 2012, 22:2572-2578.
Guo, C. et al."Discovery of Aryloxy Tetramethylcyclobutanes as Novel Androgen Receptor Antagonists", J. Med. Chem. 2011, 54, 7693-7704.
Gustafson et al., "Small-Molicule-Mediated Degradation of the Androgen Receptor through Hydrophobic Tagging", Angew. Chem. Int. Ed., 54: 9659-9662.
Gustafson, et al., "Small-Molecule-Mediated Degradation of the Androgen Receptor through Hydrophobic Tagging", Agnew Chem Int Ed., 54: 9659-9662 (2015).
Hewings, et al., "3,5-Dimethylisoxazoles Act As Acetyllysine-mimetic Bromodomain", J Med Chem. 54(19), Oct. 13, 2011, 6761-6770.
Hines, J., et al., "Posttranslational protein knockdown coupled to receptor tyrosine kinase activation with phosphoPROTACs", Proc Natl Acad Sci USA 110, 8942-8947 (2013).
Hon, et al., "Structural basis for the recognition of hydroxyproline in Hlf-1 alpha by pVHL", Nature 417, Jun. 27, 2002, 975-978.
Huang, et al., (2016) "Drugging the undruggables: exploring the ubiquitin system for drug development." *Cell Res* 26(4):484-498.
Hughes, et al., (2017) "Molecular recognition of ternary complexes: a new dimension in the structure-guided design of chemical degraders." *Essays Biochem* 61(5):505-516.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by Protacs," Curr. Protoc. Chem. Biol., 2010, vol. 2, No. 2, pp. 71-87.
Jung, M. E. et al."Structure-Activity Relationship for Thioydantoin Androgen Receptor Antagonists for Castration-Resistant Prostate Cancer (CRPC)", J. Med. Chem. 2010, 53, 2779-2796.
Knott, Edward (1955). "Compounds containing sulphur chromophores. Part I. The action of bases on heterocyclic sulphide quarternary salts", Journal of The Chemical Society (resumed). 10.1039/jr9550000916. 949-954.
Kronke, et al, "Lenalidomide Causes Selective Degradation of IKZF1 and IKZF3 in Multiple Myeloma Cells", Science 343, 301-305 (2014).
Kurimchak, A. M. et al.,"Resistance to BET Bromodomain Inhibitors Is Mediated by Kinome Reprogramming in Ovarian Cancer", Cell Reports 16, 1273-1286 (2016).
Lai, A.C., et al., "Modular Protac Design for the Degradation of Oncogenic BCR-ABL", Angew Chem Int Ed Engl 55, 807-810 (2016).
Lai, et al., (2017) "Induced protein degradation: an emerging drug discovery paradigm." *Nat Rev Drug Discov* 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the Protac Approach: A Useful Chemical Genetic Tool", ChemBioChem vol. 8, Issue 17, pp. 2058-2062, Nov. 23, 2007.
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012.
Loven, J. et al., "Selective Inhibition of Tumor Oncogenes by Disruption of Super Enhancers", Cell, 153 (2013) 320-334.
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Lu, NZ, et al., "International Union of Pharmacology. LXV. The pharmacology and classification of the nuclear receptor superfamily: glucocorticoid, mineralocorticoid, progesterone, and androgen receptors", Pharmacol Rev. Dec. 2006;58(4):782-797. Review. PubMed PMID: 17132855.

(56) References Cited

OTHER PUBLICATIONS

Maniaci C, et al. (2017) "Homo-PROTACs: bivalent small-molecule dimerizers of the VHL E3 ubiquitin ligase to induce self-degradation." *Nat Commun* 8(1):830 1-13.
Medline Plus Trusted Health Information for You, www.nlm.nih.gov/medlineplus/cancer.html pp. 1-10, (2007).
Mertz, J.A. et al., "Targeting MYC dependence in cancer by inhibiting BET bromodomains", PNAS, 108 (2011) 16669-16674.
Min, Jung-hyun, et al., "Structure of an HIV-1-alpha-pVHL complex: hydroxyproline recognition in signaling", Jun. 7, 2002, 296: 1886-1889.
Mohler, M.L., et al., Androgen receptor antagonists: a patent review (2008-2011), Expert Opinion on Therapeutic Patents, vol. 22, No. 5. pp. 541-565, (2012).
Muller, G., et al., "Amino-Substituted Thalodomide Analogs: Potent Inhibitors of TNF-α Production", Bioorganic & Medicinal Chemistry Letters 9 (1999) 1625-1630.
Neklesa, T.K., et al., "Chemical biology: Greasy tags for protein removal", Nature 487, 308-309 (2012).
Neklesa, Targeted protein degradation by Protacs. Pharmacology & Therapeutics 174, 138-144 (2017).
Nicodeme, et al., "Suppression of inflammation by a synthetic histone mimic", Nature 468, Dec. 2, 20103, 1119-1123.
Noel, J. Kay, Abstract C244: "Development of the BET Bromodomain inhibitor OTX015", Mol Cancer Ther 2013; 12(11 Suppl); C244 1-4.
Ohoka, N. et al. Sniper(TACC3) induces cytoplasmic vacuolization and sensitizes cancer cells to Bortezomib. Cancer Sci. 108, 1032-1041 (2017).
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898.
Pepe, A. et al., "Synthesis and structure-activity relationship studies of novel dihydropyridones as androgen receptor modulators", J. Med. Chem. 2013, 56, 8280-8297.
Poutiainen, PK, et al., "Design, synthesis, and biological evaluation of nonsteroidal cycloalkane[d]isoxazole-containing androgen receptor modulators", J. Med. Chem. 55, 6316-6327 (2012).
Puissant, A. et al., "Targeting MYCN in neuroblastoma by BET bromodomain inhibition", Cancer discovery, 3 (2013) 308-323.
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, et al., (2017) "Targeted protein knockdown using small molecule degraders." *Curr Opin Chem Biol* 39:46-53.
Raina, K., et al., "Protac-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Rodriguez-Gonzalez, et al., "Targeting steroid hormone receptors for ubiquitination and degradation in breast and prostate cancer", Oncogene. 27(57), Dec. 4, 2008, 7201-7211.
Rongan, et al., Perspectives in Drug Discover and Design, Sep. 10, 2011, 1998, pp. 181-209.
Rotili, D., et al., "Photoactivable peptides for identifying enzyme-substrate and protein-protein interactions", Chem Commun (Carob) 47(5), Feb. 2011, 1488-1490.
Ruchelman, A., et al., "Isosteric analogs of lenalidominde and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1 -Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (2017).
Schiedel, M., et al., "Chemically Induced Degradation of Sirtuin 2 (Sirt2) by a Proteolysis Targeting Chimera (Protac) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Shi, J. et al., "The mechanisms behind the therapeutic activity of BET bromodomain inhabitation", Molecular cell, 54 (2014) 728-736.
Shimamura, et al. "Efficacy of BET bromodomain inhabitation in kras-mutant non-small cell lung cancer", Clinical Cancer Research 19(22), pp. 6183-6192 (2013) DOI:10.1158/1078-0432.CCR-12-3904.
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
STN transcript excerpt Nov. 24, 2017 "Compounds containing sulfur *Chromophores* v. *Complex cyanines*".
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Stuhlmiller, Timothy J., et al., "Inhibition of Lapatinib-Induced Kinome Reprogramming in ERBB2-Positive Breast Cancer by Targeting BET Family Bromodomains", Cell Reports 11, 390-404 (2015).
Sundberg, et al., Protein Interations, 2007, Springer, Chapter 4, pp. 97-141.
Toure, et al., (2016) "Small-Molecule Protacs: New Approaches to Protein Degradation." *Angew Chem Int Ed Engl* 55(6):1966-1973.
Trewartha D, Carter K. "Advances in prostate cancer treatment", Nat Rev Drug Discov. (Nov. 2013);12(11):823-824. doi: 10.1038/nrd4068. PubMed PMID: 24172327.
Turk, B. E., "Binding of thalidomide to alphal-acid glycoprotein may be involved in its inhibition of tumor necrosis factor alpha production", Proc. Natl. Acad. Sci. U.S.A. 1996, 93, 7552-7556.
Van Molle, et al., "Dissecting fragment-based lead discovery at the von Hippel-Lindau protein:hypoxia inducible factor la protein-protein interface", Chem Biol. 19(10), Oct. 26, 2012, 1300-1312.
Weinmann, H., "Cancer Immunotherapy: Selected Targets and Small-Molecule Modulators", ChemMedChem (2016), 11, 450-466.
Winter, et al., "Phthalimide Conjugation as a strategy for in vivo target protein degradation", Science, 2015 vol. 348 (6241), pp. 1376-1381 [Pub online: May 21, 2015].
Wyce, A. et al., "Inhibition of BET bromodomain proteins as a therapeutic approach in prostate cancer", Oncotarget, 4 (2013) 2419-2429.
Zengerle, et al., "Selective Small Molecule Induced Degradation of the BET Bromodomain Protein BRD4" ACS Chemical Biology, Jun. 2, 2015, vol. 10, pp. 1770-1777.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem.6b01816) (2017).

(56) References Cited

OTHER PUBLICATIONS

U.S. Appl. No. 15/477,966, filed Apr. 3, 2017, US 2017-2081784 A1.

$\Delta G_{WA \cdot A}$ $$\Delta G = \Delta G_{WA \cdot A} + \Delta G_{WB \cdot B} + \Delta G_{cross}$$

PROTEIN-PROTEIN INTERACTION INDUCING TECHNOLOGY

CROSS-REFERENCE TO RELATED APPLICATIONS

This application is a continuation of U.S. patent application Ser. No. 15/477,966, titled "PROTEIN-PROTEIN INTERACTION INDUCING TECHNOLOGY", filed 3 Apr. 2017, and published as U.S. Patent Application Publication No. 2017/0281784 A1, which claims the benefit of and priority to U.S. Provisional Patent Application Ser. No. 62/318,630, titled "PROTEIN-PROTEIN INTERACTION INDUCING TECHNOLOGY", filed on 5 Apr. 2016, each of which is hereby incorporated herein by reference in its entirety for all purposes.

BACKGROUND

1. Field of the Discovery

The present disclosure relates to the field of designing compounds to modify protein activity or behavior, such as for example, by inducing protein-protein interactions, antagonizing or agonizing protein function, and/or impacting their ability to associate with partners, modifying their conformational stability, effectuating ubiquitination and degradation, or causing them to undergo other post-translational modifications including phosphorylation, dephosphorylation and other modifications. Modification of protein activity or behavior can lead to changes in, e.g., transcriptional activities, cell proliferation and/or differentiation, apoptosis.

2. Background

Designing small molecule compounds or ligands to bind to a protein and thus block the function of that protein is a highly desired approach for developing drugs for pharmaceutical applications. However, many proteins are considered undruggable because they lack binding pockets deep enough to allow development of high affinity compounds, and high affinity is a prerequisite for in vivo efficacy and specificity in many cases. The particular examples include, but not limited to, receptor proteins and scaffolding proteins, which do not have enzymatic active sites and only have interaction surfaces for associating with protein or non-protein partners.

There exists an ongoing need for a technology that facilitates drug design. In particular, it is desirable to design compounds in which one ligand molecule is used to simultaneously target two protein molecules (of the same protein or different proteins), the ligand molecule induces protein-protein interaction, and the protein-protein interaction energy gained in this process enhances the potency of the ligand.

SUMMARY

The present disclosure provides a Protein-Protein Interaction Inducing Technology (PPIIT), which allows one to design potent ligands for "undruggable" targets, or proteins with only shallow binding sites. The present disclosure is based on the surprising and unexpected discovery that a ligand molecule with certain characteristics is able to bind to two protein molecules simultaneously and recruit them to form a transient or stable protein-protein interaction complex. The protein-protein interaction and other cross-domain interactions gained in this process contribute additional stabilization energy to the complex beyond the combination of the binary binding energies, and therefore, largely increase the binding potency of the ligand (FIG. 1). That is, a ligand molecule with certain characteristics provides a protein-protein interaction between two protein molecules that is greater than one would expect given the ligands binding efficiency for either protein individually. Accordingly, the present disclosure provides a method for discovering, designing or deriving a ligand for forming a transient or stable interaction between two of the same proteins or two different proteins. The present disclosure also provides a composition that induces protein-protein interactions between, e.g., two of the same proteins or two different proteins, and the use thereof.

An aspect of the disclosure provides a ligand L able to induce protein-protein interactions between protein A (a first protein) and protein B (a second protein). In an embodiment, the ligand has a generic chemical structure of WA-C-WB, wherein the WA is a warhead (e.g., a chemical group or moiety) targeting protein A, the WB is a warhead targeting protein B, and C is a connector (e.g., a chemical group or moiety) providing appropriate spacing between WA and WB. C is covalently linked to WA and WB. The distance or the range of distance between WA and WB in the tripartite molecule WA-C-WB is critical for the protein-protein interaction between the protein A and protein B to occur, and the lengths of C allowing optimal or desirable protein-protein interactions depend upon the structures of protein A and protein B involved. In an embodiment, C has a chain length or number of atoms in a range of 0 to 30 atoms, e.g., the C chain length can be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 atoms. In certain embodiments, the chain is substituted or unsubstituted. That is, in an embodiment, the connector is 0 atoms and the ligand L has a general structure of WA-WB. Therefore, the present disclosure also relates a method to determine a length and other structural features of the connector C so that the tripartite ligand WA-C-WB, after it binds protein A and protein B with the respective warheads, allows protein A and protein B to interact with each other favorably and optimally (i.e., the connector provides the ligand with a binding efficiency greater than the warheads WA and WB provide individually).

In an additional aspect, the disclosure provides a method for determining whether or not a ligand L induces a protein-protein interaction between protein A and protein B. In an embodiment, the method includes quantifying and comparing a ternary binding potency (A·L·B) and a corresponding binary binding potency. In a particular embodiment, the ternary binding potency is the $IC_{50}$ or a total concentration of the ligand at which the concentration of a ternary complex A·L·B is half of its maximum value, determined by varying the concentration of the ligand systematically. In another embodiment, a binary binding potency for A·L is the $IC_{50}$ or the total concentration of the ligand at which the concentration of the binary complex A·L is half of its maximum value, determined by varying the concentration of the ligand in the absence of a contribution of protein B. In an additional embodiment, a binary binding potency for B·L is the $IC_{50}$ or the total concentration of the ligand at which the concentration of the binary complex B·L is half of its maximum value, determined by varying the concentration of the ligand in the absence of the contribution of protein A. The protein concentrations for protein A and protein B are kept constant in the determination of the above three $IC_{50}$s for the ligand.

According to an embodiment, if the ternary $IC_{50}$ is smaller than both of the corresponding binary $IC_{50}$s, protein-protein interactions should exist.

In another aspect of the disclosure, the protein-protein interactions are determined by measuring a synergism of binding affinities. The binding constant between protein A and ligand L can be measured in the absence or in the presence of the contribution of protein B. In an embodiment, if the binding constant between protein A and ligand L is smaller (i.e., has a higher affinity) in the presence of the contribution of protein B than in the absence of the contribution of B, the existence of protein-protein interactions between protein A and protein B can be assumed. Similarly, a binding constant between protein B and ligand L can be measured in the absence or in the presence of the contribution of protein A. In another embodiment, observing a strengthening of binding of protein B and ligand L by protein A signals the existence of protein-protein interactions.

In an aspect of the disclosure, the existence of protein-protein interactions between protein A and protein B mediated by ligand L can be demonstrated by performing molecular dynamics (MD) simulation. That is, in an embodiment, the method comprises performing an MD simulation. In a particular embodiment, the MD simulation is performed on a starting conformation of a ternary model A·L·B, wherein the warheads of the ligand L occupy the corresponding binding sites of protein A and protein B and the connector of ligand L assumes an extended or arbitrary conformation. The MD simulation with explicit water can lead to a complex in which protein A physically interacts with protein B and/or the B-binding warhead of the ligand L or protein B physically interacts with protein A and/or the A-binding warhead of the ligand L.

In additional embodiments, the protein-protein interaction of the present disclosure includes at least one of ion-pair, hydrogen bonding, and hydrophobic interactions, and/or the formation of hydrophobic clusters contributed by the non-polar groups of different proteins and ligand molecules. In another embodiment, the A-L-B ternary system adopts an arrangement that includes interactions between at least one of: the two warheads WA and WB of a single ligand, protein A and WB, protein B and WA, and the proteins and the connector C. Like the pure protein-protein interaction, these cross-domain interactions involving parts of a ligand can also contribute extra binding energy beyond the combination of the binary binding energies (i.e., stemming from the docking of the warheads to the respective binding sites). As used herein, the term "protein-protein interaction" can refer to, unless explicitly stated otherwise or by the context of its use, these cross-domain interactions as well as pure protein-protein interactions.

In one embodiment, the present disclosure provides a method to find the connector C for a tripartite ligand L of chemical structure WA-C-WB to induce protein-protein interaction between A and B. In an embodiment, WA and WB are chemical moieties known to bind to A and B, respectively, and C is a linear chain of carbon atoms or a linear chain of alternating carbon atoms and heteroatoms. In a particular embodiment, any two heteroatoms are separated by at least two carbon atoms, thereby producing a chemically stable compound. In some embodiments, the method includes synthesizing a set of compounds in which the length of the connector C is systematically varied by changing the number of atoms constituting C, and WA and WB remain constant. In an embodiment, the length of connector C is varied within a range between 0 and 30 atoms, wherein the incremental differences in length can be between 1 to 3 atoms. However, other ranges and increments of exploration are possible. In certain embodiments, the method comprising synthesizing ligands with different attachment points on WA and WB to link the connector C. In another embodiment, once attachment points on WA and WB to link the connector C is determined, the length of the connector C can be examined, as discussed above, with the new attachment points. This process of changing attachment points and exploring the length of connector C can be repeated to find ligands that produce greater protein-protein interactions. Each compound in the process is measured to determine and compare its ternary binding potency and binary binding potencies. Embodiments of the disclosure can determine which ranges of connector length and which attachment points correspond to best ternary binding potencies, and whether or not any of the ternary binding potency values are more potent than the corresponding binary binding potency values, thereby indicating the existence of the protein-protein interaction. Whether or not significantly favorable protein-protein interactions can be found for a given protein or protein pair using this process depends on the nature of the proteins involved, but embodiments of the disclosure provides a system to efficiently determine ligands that can provide favorable protein-protein interactions.

Embodiments of the method can result in a ligand L (compound) wherein the connector C contains no atoms. That is, the compound(s) can have a bi-functional chemical structure of WA-WB, wherein the two warheads are directly linked with a covalent bond or fused through a common bond. Some protein pairs can adopt such an interaction mode that allows close approach between WA and WB so that compounds like WA-WB are suitable to mediate the interactions between protein A and protein B.

The protein pair A and B between which the interactions are sought can be different proteins or the same protein. In embodiments where proteins A and B are identical (i.e., the same proteins), the two warheads WA and WB of the ligand of type WA-C-WB or WA-WB can be identical or different as long as they are able to bind to the corresponding targets. The method to measure the protein-protein interaction can be the same as described previously or can be inferred directly from the previous description for the case where protein A and protein B represent different proteins.

The present disclosure provides compounds that can induce protein-protein interactions between protein pairs that do not naturally interact. The present PPIIT process was applied to the following protein pairs and induced favorable protein-protein interactions between each of the pairs: androgen receptor (AR) with von Hippel-Lindau protein (VHL), AR with cereblon, estrogen receptor (ER) with VHL, bromodomain-containing protein 4 (BRD4) with VHL, and BRD4 with cereblon. These pairs are not known to interact with each other naturally. Embodiments of the present disclosure can also be used to strengthen the interactions between protein pairs that do interact with each other naturally.

In an embodiment, the present disclosure provides a process to optimize a ligand L which has measurable capability of inducing protein-protein interaction between protein A and protein B. The ligand can have recognizable warheads WA and WB for targeting protein A and protein B, respectively. In particular embodiments, the generic chemical structure of the ligand is WA-C-WB in which C is a connector covalently linked to WA and WB, or WA-WB in which WA and WB are covalently linked. Some embodiments of the present disclosure include modifying the chemical structure of the ligand to change its ability to induce protein-protein interactions and/or other characteristics related to its chemical structure. In an embodiment, the process of optimization comprises building or synthesizing an initial molecular model for the ternary complex A·L·B in which the warheads of the ligand L occupy the corresponding binding sites of protein A and protein B, respectively. The crystal structures or validated models of complexes of A·L and B·L can be useful input to determine how the warheads dock onto protein A and protein B. In a particular embodiment, the method includes performing MD simulation with explicit water on the initial model of ternary complex and a representative conformation is derived from the simulation trajectory. The representative conformation can be used to redesign the connector and/or modify the warheads.

The present description also provides a composition useful for inducing protein-protein interactions. The composition comprises a compound or composition that is derived from the compound exploration or design processes described above. In an embodiment, the composition has a generic chemical structure of WA-C-WB in which WA and WB are warheads targeting protein A and protein B, respectively, and C is a connector covalently linked to WA and WB. WA and WB can be known ligands of protein A and protein B or they can also be derived using established technologies in the art such as high-throughput screening and/or structure-based drug design. In one embodiment, C is a linear chain of carbon atoms or a linear chain of alternating carbon atoms and heteroatoms and the length of the connector C as well as the attachment points on WA and WB are derived using the exploration process described previously. In another embodiment, C contains branched groups, saturated rings, and/or non-saturated rings, each with or without heteroatoms. In yet another embodiment, the connector C is reduced to zero so that the composition has a generic structure of WA-WB in which the two warheads are directly linked together through a covalent bond, sharing a common atom, or sharing a common bond (i.e., fusion).

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

BRIEF DESCRIPTION OF THE FIGURES

(FIG. 1A): Protein A has a shallow binding site so that only weakly associating small molecule binders can be found or designed to associate with protein A. (FIG. 1B): A tripartite or bi-functional compound can be designed to recruit two protein molecules together to form a transient or stable complex. The protein-protein interaction and other cross-domain interactions gained in this process contribute additional stabilization energy to the complex beyond the combination of the binary binding energies, and thus largely increase the potency of the compound (i.e., the ability of the compound to bind protein A and protein B). This technology can work to induce either homodimer (A and B are the same protein) or heterodimer (A and B are different proteins) depending upon the design of the warheads of the tripartite or bi-functional compound. The connector length of the tripartite compound needs to be in the correct range in order for a favorable protein-protein docking pose to be found.

DETAILED DESCRIPTION

Figure 1A:
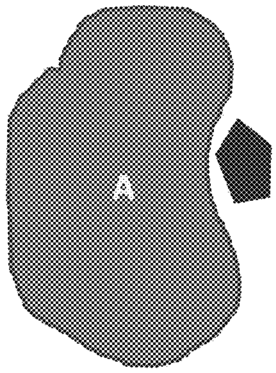
FIG. 1A and FIG. 1B illustrate the general concept of the Protein-Protein Interaction Inducing Technology (PPIIT).

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

The present disclosure relates to a method of designing compounds (compositions) that induce protein-protein interactions between a given pair of protein molecules A (i.e. protein A) and B (i.e. protein B), wherein protein A and protein B can be two different proteins or two of the same proteins. The present disclosure also provides a composition or the characteristics of a composition capable of inducing said protein-protein interaction.

As such, in certain aspects the description provides methods of designing a bifunctional compound capable of effectuating protein-protein interactions between a first protein molecule (A) and a second protein molecule (B), the method comprising: (a) providing a bifunctional ligand (L) of structure WA-$C_n$-WB, wherein WA is a warhead targeting the first protein A, WB is a warhead targeting the second protein B, and C is a connector with length or number of atoms n, covalently linked to WA and WB; (b) measuring the ternary binding potency and the binary binding potencies of the ligand L with respect to the first protein A and the second protein B; and (c) determining the capability of the ligand to induce an interaction between the first protein A and the second protein B.

In any of the aspects or embodiments described herein, at least one of the warhead WA, warhead WB, and connector C is a chemical group or moiety. In any of the aspects or embodiments described herein, the warheads WA and WB are derived from compounds known to bind to proteins A and B, respectively.

In any of the aspects or embodiments described herein, the connector C is a linear chain of carbon atoms or a linear chain of alternating carbon atoms and heteroatoms. In any of the aspects or embodiments described herein, any two heteroatoms are separated by at least two carbon atoms.

In any of the aspects or embodiments described herein, the method of designing the bi-functional ligand further comprises a step of modifying the chain length or the number of atoms of the connector C to determine the appropriate chain length or number of atoms for inducing protein-protein interactions, determining comprising.

In any of the aspects or embodiments described herein, the method includes the steps of (a) synthesizing a set of compounds with the number of atoms in C varying n between 0 and 30 while keeping the warheads WA and WB constant; (b) measuring the binding of each compound to determine which compounds have a superior ternary binding potency relative to a corresponding binary binding potency for proteins A and B; and (c) determining the n values that give rise to the potencies indicative of the existence of protein-protein interactions.

In any of the aspects or embodiments described herein, determining the chain length or the number of atoms of the connector C (n) further comprises the step of changing the attachment points on WA and WB that are used to link the warheads to the connector C, and repeat steps (a) through (c) to find additional compounds with protein-protein interactions.

In any of the aspects or embodiments described herein, connector C is a chain with branched groups and/or contains rings.

In any of the aspects or embodiments described herein, the measuring step further comprises: measuring the influence of the first protein or the second protein on a binding constant of another protein toward the ligand to evaluate the capability of the ligand L to induce the protein-protein interaction.

In any of the aspects or embodiments described herein, the method comprises a step of: performing molecular dynamics simulations to demonstrate protein-protein interactions and other cross-domain interactions in ternary systems composed of the first protein A, the second protein B, and the ligand L to evaluate the capability of the ligand L to induce the protein-protein interaction.

In any of the aspects or embodiments described herein, the first protein A and the second protein B are the same protein. In any of the aspects or embodiments described herein, the first protein A and the second protein B are different proteins.

In any of the aspects or embodiments described herein, the method further comprises selecting a ligand with a ternary complex that results in surface area burial greater than the sum of the surface area burial of the corresponding warhead monomers with the first and second proteins.

In another aspect, the description provides a compound resulting from performing a method as described herein.

In another aspect, the description provides a compound for use in treating or preventing a disease or disorder, administering an effective amount of a compound as described herein to a person in need thereof.

In another aspect, the description provides a method of designing a tripartite or bifunctional ligand that induces protein-protein interaction(s) between a first protein molecule (A) and a second protein molecule (B), the method comprising: designing, preparing, and/or synthesizing a plurality of tripartite and/or bifunctional compounds with the general structure WA-C-WB or WA-WB, wherein WA is a warhead that associates with the first protein, WB is a warhead that associates with the second protein, and C is a connector covalently linked or bound to WA and WB; designing, preparing, and/or synthesizing control compounds; quantifying induced protein-protein interactions with at least one of biochemical assays, cellular assays, and molecular dynamics simulations; and selecting the tripartite or bifunctional compound/ligand that induces protein-protein interactions and/or other cross-domain interactions in the ternary complex.

In any of the aspects or embodiments described herein, designing, preparing, and/or synthesizing includes varying a length of the connector between 0 atoms to 30 atoms while maintaining the same warheads and connection points between the connector and the warheads. In any of the aspects or embodiments described herein, the length of the connector is varied by an increment of 1 to 3 atoms. In any of the aspects or embodiments described herein, the covalent link between the connector and WA and/or WB is at a solvent-exposed point.

In any of the aspects or embodiments described herein, the plurality of tripartite and/or bifunctional compounds comprises subsets of compounds having a unique covalent link between warhead WA and warhead WB or a unique series of covalent links between warhead WA, the connector, and warhead WB, relative to the other subsets.

In any of the aspects or embodiments described herein, designing, preparing, and/or synthesizing control compounds comprises modifying either warhead WA or WB such that substantially all of its association/binding ability to protein A or protein B is removed.

In any of the aspects or embodiments described herein, quantifying protein-protein interactions using biochemical assays comprises determining whether (i) the tripartite or bifunctional compound binding/associating with protein A and protein B produce synergism, or (ii) the tripartite or bifunctional compound/ligand induces ternary binding potency.

In any of the aspects or embodiments described herein, selecting the tripartite or bifunctional compound/ligand that induces protein-protein interactions in the ternary complex comprises: selecting at least one tripartite or bifunctional compound/ligands that have a ratio α that is greater than about 1, wherein the ratio α is $IC_{50}^{A}$ over $IC_{50}^{A/B}$ or $IC_{50}^{B}$ over $IC_{50}^{B/A}$; and/or selecting at least one tripartite or bifunctional compounds/ligands that have a ratio αT that is greater than about 1, wherein the ratio αT is a ratio of the lower of $IC_{50}^{A}$ and $IC_{50}^{B}$ over $IC_{50}^{T}$.

In any of the aspects or embodiments described herein, quantifying induced protein-protein interactions comprises performing molecular dynamics simulations on tripartite and/or bifunctional compounds that are determined to induce protein-protein interaction(s) by either biochemical assays or cellular assays.

In any of the aspects or embodiments described herein, the protein-protein interactions for a particular conformation determined by molecular dynamics simulations are examined by calculating at least one of atom distances, surface area burial, and interaction energies for the ternary complex formation and a binary complex formation.

In any of the aspects or embodiments described herein, the protein-protein interactions for a particular conformation determined by molecular dynamics simulations are examined along the simulation trajectory and the critical distances related to the interactions and the intermolecular energies between critical groups can be calculated along the simulation time.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Figure 1B:
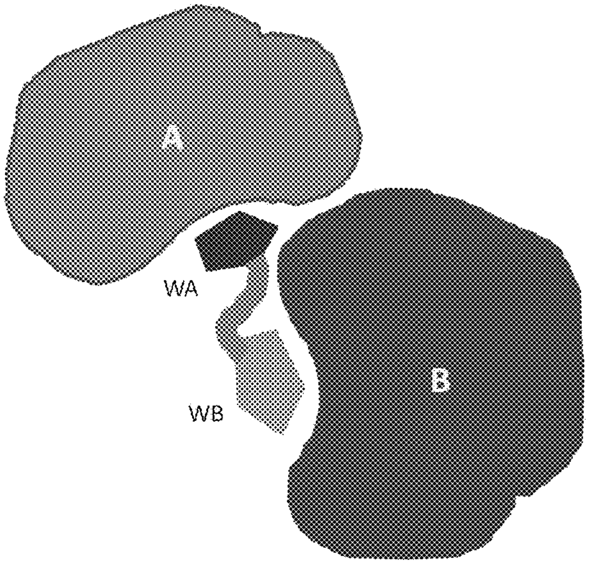

FIG. 1A and FIG. 1B illustrates a ligand of the present disclosure. The ligand is able to induce protein-protein interactions between two protein molecules and has a generic chemical structure of WA-C-WB. WA is a warhead that targets protein molecule A (e.g., binds or interacts with protein molecule A). WB is a warhead that targets protein molecule B (e.g., binds or interacts with protein molecule B). C is a connector that provides appropriate spacing between warhead WA and warhead WB. In a particular embodiment, the connector C is covalently linked to warhead WA and warhead WB.

Figure 2:
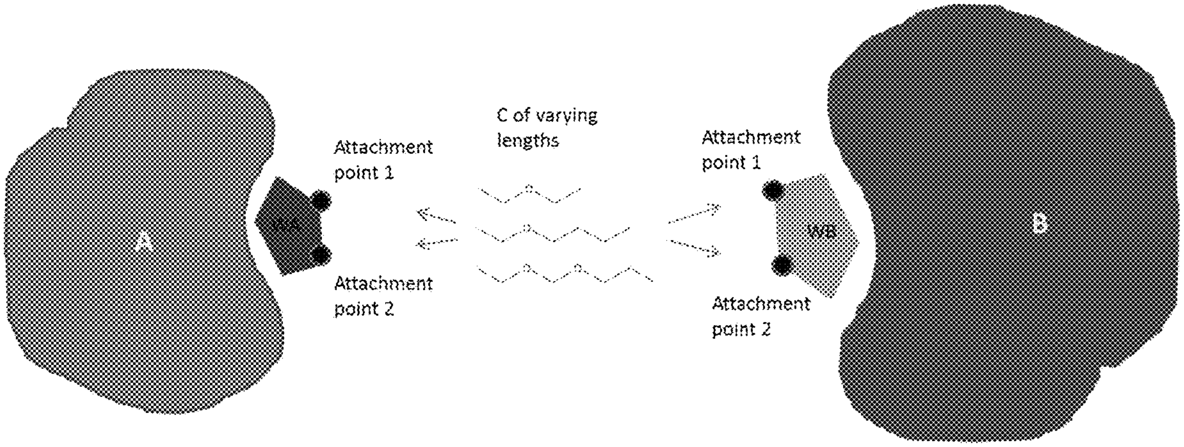
FIG. 2 is an illustration of a general concept of examining connectors of differing lengths and different connection points (or links) with WA and WB to optimize the tripartite compound's ability to induce protein-protein interactions or other cross-domain interactions. A similar technique can be used to optimize a bifunctional compound/ligand.

As shown below, the distance or the range of the distance between warhead WA and warhead WB in the tripartite molecule WA-C-WB is critical for the protein-protein interaction between protein A and protein B to occur, and the lengths of the connector C associated with optimal or desirable protein-protein interactions depend upon the structures of protein A and protein B involved (FIG. 2). Therefore, a major part of the present disclosure relates to a process of chemical exploration to identify an appropriate connector C. In an embodiment, the warhead WA and/or warhead WB is a known ligand of protein A and/or protein B. In another embodiment, warhead WA and/or warhead WB is derived using established technologies in the art, for example, a high-through screening and/or structure-based drug design may be utilized to discover/derive a previously unknown ligand for protein A and/or protein B. In some embodiments, for certain proteins A and B, a ligand of generic chemical structure of WA-WB is appropriate to induce the corresponding protein-protein interaction, wherein no connector is needed and the warheads are linked directly through a covalent bond, a common atom, or fused together through a common bond.

In an aspect of the present disclosure, a method of designing tripartite or bifunctional compounds is provided. The method comprises: designing, preparing, and/or synthesizing a plurality of tripartite and/or bifunctional compounds (i.e., ligands) with the general structure WA-C-WB or WA-WB; designing, preparing, and/or synthesizing control compounds; and quantifying induced protein-protein interactions with at least one of biochemical assays, cellular assays (i.e. in a cellular context), and molecular dynamics simulations; and selecting the tripartite or bifunctional compound/ligand that induces protein-protein interactions and/or other cross-domain interactions in the ternary complex.

WA selectively binds protein A and WB selectively binds protein B. The warheads WA and WB can be independently either known association/binding partners of protein A and protein B, respectively, or they can be selected through a conventional high throughput screening and/or structure-based drug design. Proteins A and B can be the same protein or be two different proteins. In an embodiment, WA and WB are linked to connector C via covalent bonds. In another embodiment, WA and WB are directly linked through a common bond, a common atom, or fused together through a common bond.

In certain embodiments, designing, preparing, and/or synthesizing includes varying a length of the connector. That is, the connectors of the plurality of tripartite and/or bifunctional compounds vary in length, i.e. the number of atoms along its length (n) are different, while the connectors of each of the plurality of tripartite and/or bifunctional compounds are linked in the same fashion to the same WA and WB. This allows for determination of the optimal connector length to induce protein-protein interactions. In an embodiment, the length of the connector is varied between 0 to 30 atoms. In a particular embodiment, the length of the connector is varied by an increment of 1-6 atoms, 1-5 atoms, 1-4 atoms, 1-3 atoms, 1-2 atoms, 2-6 atoms, 2-5 atoms, 2-4 atoms, 2-3 atoms, 3-6 atoms, 3-5 atoms, 3-4 atoms, 4-6 atoms, 4-5 atoms, or 5-6 atoms. In an embodiment, the connector is varied by an increment of 1, 2, 3, 4, 5, 6, 7, 8, 9, or 10 atoms. In certain embodiments, the connector chain is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 atoms, and may be substituted or unsubstituted.

In other embodiments, the connector is linked to WA and/or WB via a solvent-exposed point. In some embodiments, the plurality of tripartite and/or bifunctional compounds comprises subsets of compound in which each subset of compounds has a unique link relative to the other subsets. That is, each subset of compounds has a unique set of attachment points between WA, WB and the connector, and/or WA and WB. Furthermore, each subset with a unique link comprises a plurality of tripartite and/or bifunctional compounds, each having a unique connector for the subset of compounds. In an embodiment, each of the compounds of the subset has a connector of a different length within the range of 0 to 30 atoms.

In particular embodiments, designing, preparing, and/or synthesizing control compounds comprises modifying either WA or WB such that substantially all of its association/binding ability to protein A or protein B, respectively, is removed. For example, WA would retain its ability to associate with or bind protein A, while WB would be modified such that WB* substantially lacks the ability to associate with or bind protein B, or vise versa (please note that an asterisk denotes a WA or WB wish substantially diminished or eliminated ability to bind or associate with protein A or protein B). The ability for WA or WB to associate/bind with its respective protein can be diminished/eliminated by, for example, adding a methyl group to cause clashes with the association/binding pocket of the warhead or inverting at least one chiral center that is critical for the association/binding. Production of the control compounds allow for the examination for induced protein-protein interactions while accounting for membrane permeability difference that would exist if WA or WB were removed from the compound. As discussed below, these modified tripartite or bifunctional compounds allow for measurement of binary binding potencies, which can be compared with measured ternary binding potency of the parent tripartite or bifunctional compound in cellular assays to determine whether the parent tripartite or bifunctional compound induced protein-protein interactions.

In some embodiment, quantifying protein-protein interactions using biochemical assays comprises determining whether (i) the tripartite or bifunctional compound binding/associating with protein A and protein B produce synergism (i.e. whether the binding potency of the compound/ligand to protein A or protein B is strengthened by the presence of the association/binding of the other protein (protein B or protein A, respectively) to the compound/ligand) or (ii) the tripartite or bifunctional compound/ligand induces ternary binding potency (i.e. the tripartite or bifunctional compound/ligands ability to produce ternary species).

In an embodiment, determining whether the compound/ligand produces synergism includes comparing binary binding potencies of binary control compounds, i.e. WA-C and C-WB (for tripartite compounds/ligands) or WA and WB (for bifunctional compounds/ligands), with the binding potency of its respective tripartite or bifunctional compound ligand (i.e., WA-C-WB or WA-WB). The binary binding potencies of binary control compounds are a measure of the binding potency between each warheads and its associated protein. The binary binding potency of a tripartite or bifunctional compound with respect to A, or the binary binding $IC_{50}^{A}$, can be determined by titrating the corresponding mono-functional compound WA-C-WB* or WA-WB* (as discussed above, an asterisk denotes a warhead WA or WB with substantially diminished or eliminated capacity/ability to bind to protein A or protein B) into a solution of A. A dose-response curve reflective of the complex formation between compound WA-C-WB* or WA-WB* and the protein A is measured as a function of the compound concentration. In an embodiment, the $IC_{50}^{A}$ is the total compound concentration at which the response reaches a half height of its maximum.

In a similar fashion, the binary binding potency of a tripartite or bifunctional compound with respect to B, or the binary binding $IC_{50}^{B}$, can be determined by titrating the corresponding mono-functional compound WA*-C-WB or WA*-WB into a solution of B and measuring the dose-response curve reflective of the complex formation between protein B and compound WA*-C-WB or WA*-WB. In an embodiment, the $IC_{50}^{B}$ is the total compound concentration at which the response reaches a half height of its maximum. When protein A and protein B are the same protein, and warheads WA and WB are identical, $IC_{50}^{A}$ and $IC_{50}^{B}$ are the same. When protein A and protein B are different proteins, $IC_{50}^{A}$ can be determined by titrating the compound WA-C-WB or WA-WB into the solution of A without protein B, and/or $IC_{50}^{B}$ can be determined by titrating the compound WA-C-WB or WA-WB into the solution of B without protein A.

The binding potency of the tripartite or bifunctional compound/ligand can be examined relative to protein A or protein B. For example, the binding potency of the tripartite or bifunctional compound/ligand can be measured by titrating the compound into a solution of mixture of protein A and protein B. A dose-response curve reflective of the complex formation between the compound and protein A can be measured as a function of the compound concentration. $IC_{50}^{A/B}$ is the total compound concentration at which the response between the compound and protein A reaches a half height of its maximum, and which includes the contributions of the binary complex A-L and ternary complex A-L-B. Similarly, a dose-response curve reflective of the complex formation between the compound and protein B can be measured as a function of the compound concentration. $IC_{50}^{B/A}$ is the total compound concentration at which the response between the compound and protein B reaches a half height of its maximum, and which includes the contributions of the binary complex B-L and ternary complex A-L-B. If A and B are identical (i.e., the same protein), $IC_{50}^{A/B}=IC_{50}^{B/A}$ and can be determined by titrating the compound into the solution of the proteins.

In an embodiment, comparing binary binding potencies of binary control compounds with the binding potency of its respective tripartite or bifunctional compound ligand comprises producing a ratio $\alpha$ of the binary $IC_{50}^{A}$ over $IC_{50}^{A/B}$. In another embodiment, the ratio $\alpha$ is of the binary $IC_{50}^{B}$ over $IC_{50}^{B/A}$. When the same protein concentrations are used to determine the ratio $\alpha$: there is substantially no interaction between protein A and protein B when $\alpha$ is about 1, there is a favorable interaction between protein A and protein B (i.e. a favorable protein-protein interaction) when $\alpha$ is greater than about 1, and there is an unfavorable interaction between protein A and B (i.e., an unfavorable protein-protein interaction) when $\alpha$ is less than about 1.

In an embodiment, determining whether the tripartite or bifunctional compound/ligand induces ternary binding potency comprises comparing binary binding potencies of binary control compounds, i.e. WA-C and C-WB (for tripartite compounds/ligands) or WA and WB (for bifunctional compounds/ligands), with a ternary binding potency (i.e., WA-C-WB or WA-WB). The binary binding potencies can be determined as described above. The ternary binding potency can be determined by titrating the tripartite or bifunctional compound/ligand into a solution of a mixture of proteins A and B, and producing a dose-response curve reflective of the ternary complex formation A-L-B measured as a function of the compound concentration. Ternary binding $IC_{50}^{T}$ is the total compound concentration at which the response first reaches a half height of its maximum value (i.e. the earliest occasion). In another embodiment, comparing binary binding potencies of binary control compounds with a ternary binding potency comprises producing a ratio $\alpha^{T}$ of the lower value of binary binding $IC_{50}^{A}$ and $IC_{50}^{B}$ over the ternary binding $IC_{50}^{T}$. When the same protein concentrations are used to determine $IC_{50}^{T}$ and $IC_{50}^{A}$ or $IC_{50}^{B}$: there is a favorable interaction between protein A and protein B (i.e. a favorable protein-protein interaction) when $\alpha^{T}$ is greater than about 1, there is an unfavorable interaction between protein A and B (i.e., an unfavorable protein-protein interaction) when $\alpha^{T}$ is less than or equal to about 0.1; and there is a moderate or no protein-protein interaction between protein A and protein B when $\alpha^{T}$ is in a range of about 0.1 to about 1.

Quantifying the induced protein-protein interactions with cellular assays (i.e. in a cellular context) can comprise determining whether (i) the tripartite or bifunctional compound binding/associating with protein A and protein B produce synergism, or (ii) the tripartite or bifunctional compound/ligand induces ternary binding potency. In an embodiment, when examining synergism, a binary binding potency and a ternary binding potency are determined in a cellular assay. In a particular embodiment, comparing the binary binding potency with the ternary binding potency includes producing a ratio α selected from: $IC_{50}^{A}/IC_{50}^{A/B}$ and $IC_{50}^{B}/IC_{50}^{B/A}$.

The ratios can be determined as follows. Binary binding $IC_{50}^{A}$ between a tripartite or bifunctional compound and protein A can be determined by, for example, titrating a tripartite or bifunctional compound substantially lacking the ability to bind/associate with protein B (e.g., WA-WB* or WA-C-WB*) into a medium with cells that express protein A and protein B, and producing a dose-response curve reflective of the complex formation between the compound and protein A in the cells, measured as a function of the compound concentration. As such, $IC_{50}^{A}$ is the total compound concentration at which the response reaches a half height of its maximum. The binary binding $IC_{50}^{B}$ between a tripartite or bifunctional compound and protein B can be determined by, for example, titrating a tripartite or bifunctional compound substantially lacking the ability to bind/associate with protein A (e.g., WA*-WB or WA*-C-WB) into a medium with cells that express protein A and protein B, and producing a dose-response curve reflective of the complex formation between the compound and protein B in the cells, measured as a function of the compound concentration. As such, $IC_{50}^{B}$ is the total compound concentration at which the response reaches a half height of its maximum. When protein A and protein B are the same protein and the two warheads WA and WB are identical, $IC_{50}^{A}$ and $IC_{50}^{B}$ are not differentiable and the two determinations become one.

The binding potency of the tripartite or bifunctional compound to protein A in the presence of the contribution of protein B, i.e. $IC_{50}^{A/B}$, can be determined by, for example, titrating the tripartite or bifunctional compound/ligand (i.e. WA-C-WB or WA-WB) into a medium with cells that express protein A and protein B, and producing a dose-response curve reflective of the complex formation between the compound/ligand and protein A in the cells, measured as a function of the compound concentration (the contributions are from binary species A-L and ternary species A-L-B). As such, the $IC_{50}^{A/B}$ is the total compound/ligand concentration at which the response reaches half the height of its maximum. The binding potency of the tripartite or bifunctional compound and protein B in the presence of the contribution of protein A, i.e., $IC_{50}^{B/A}$, can be determined by, for example, titrating the tripartite or bifunctional compound ligand into a medium with cells that express protein A and protein B, and producing a dose-response curve reflective of the complex formation between the compound/ligand and protein B in the cells, measured as a function of the compound concentration (the contributions are from binary species B-L and ternary species A-L-B). As such, the $IC_{50}^{B/A}$ is the total compound/ligand concentration at which the response reaches half the height of its maximum. When protein A and protein B are the same protein and the two warheads WA and WB are identical, $IC_{50}^{A/B}$ and $IC_{50}^{B/A}$ are not differentiable and the two determinations become one.

The ratios of $IC_{50}^{A}/IC_{50}^{A/B}$ and $IC_{50}^{B}/IC_{50}^{B/A}$ should converge so either may be used as the ratio α. When the membrane permeability of the control compounds (e.g., WA*-C-WB, WA-C-WB*, WA*-WB, or WA-WB*) are the same or similar to that of the tripartite or bifunctional compound, the ratio α is independent of the membrane permeability of the compound and is a measure of the interactions between proteins A and B in the ternary complex with the compound. As such, the ligand induces: a favorable protein-protein interaction between protein A and protein B when α is greater than about 1; an unfavorable protein-protein interaction between protein A and protein B when α is less than about 1; and no protein-protein interaction between protein A and protein B when α is about 1.

The ternary binding potency of the tripartite or bifunctional compound to protein A and protein B can be determined by titrating the compound into medium with cells expressing protein A and protein B, and producing a dose-response curve reflective of ternary species formation, such as A-L-B. Ternary binding $IC_{50}^{T}$ can be the total compound concentration at which the response first reaches half the height of its maximum (i.e. the first occasion it reaches half the height of its maximum). In an embodiment, $\alpha^{T}$ is a ratio of the smaller binary binding $IC_{50}^{A}$ and $IC_{50}^{B}$ over the ternary binding $IC_{50}^{T}$. The value $\alpha^{T}$ is independent of membrane permeability of the compounds because of the cancelation of the effect by the parent tripartite or bifunctional compound and the control compounds. As such, the ligand induces: a favorable protein-protein interaction between protein A and protein B when $\alpha^{T}$ is greater than about 1; an unfavorable protein-protein interaction between protein A and protein B when $\alpha^{T}$ is less than or equal to about 0.1; and moderate or no protein-protein interaction between protein A and protein B when α is in a range of about 0.1 to about 1.

In an embodiment, quantifying the induced protein-protein interactions with molecular dynamics simulations comprises: building an initial model of a ternary complex of the tripartite or bifunctional compound/ligand with protein A and protein B (i.e., A-L-B, A-WA-WB-B, A-WA-C-WB-B, etc.) by docking protein A with WA and protein B with WB. In particular embodiment, docking of protein A and protein B is guided by existing crystal structures for binary complexes (e.g., WA-A or WB-B). In another embodiment, docking of protein A and protein B is performed by a docking program. In an embodiment, at least one of the following characteristics is used: (i) a connector conformation is set to an extended conformation arbitrarily; (ii) the system is solvated with explicit waters and counter ions in about 0.1 M sodium chloride; (iii) the molecular dynamics simulation is performed on the system for a 40 nanoseconds production time; (iv) coordinate frames from the last 10 nanoseconds of simulation are subject to clustering analysis; and (v) a frame closest to the center of a largest cluster is considered as the most populated conformation and used as a representative conformation of the system. In some embodiments, at least two, three, four, or all five of the characteristics are used.

In an embodiment, protein-protein interactions and other cross-domains interactions for a particular conformation are examined by calculating at least one of atom distances, surface area burial, and interaction energies (e.g. on a group-to-group basis) for the ternary complex formation and a binary complex formation. In another embodiment, protein-protein interactions and other cross-domain interactions are monitored along the simulation trajectory and the critical distances related to the interactions and the intermolecular energies between critical groups can be calculated along the simulation time.

As such, selecting the tripartite or bifunctional compound/ligand that induces protein-protein interactions and/or other cross-domain interactions in the ternary complex can be achieved by selecting the compound that demonstrates synergism and/or ternary binding potency that is greater/strengthened relative to the value predicted by binary binding potency, as described above.

Furthermore, in an embodiment, any compound with an $\alpha$ value or $\alpha^T$ value that demonstrates there is a protein-protein interaction or other cross-domain interactions is subject to molecular dynamics simulation, e.g. as described above. The simulation can therefore reveal how the ligand, protein A, and protein B interact with each other to induce the cross-domain interactions. In some embodiment, the representative conformation of the ternary complex from the molecular dynamics simulations have a trimer conformation (i.e., ternary conformation) in which protein molecules A and B form a complex that has a collective binding site for the compound/ligand. In an embodiment, part or all of the connector interacts with the rest of the solute system and contributes to the stability of the ternary complex. The representative conformation of the ternary complex is used to guide optimization of the compound.

In additional embodiments, designing, preparing, and/or synthesizing a plurality of tripartite and/or bifunctional compounds can include making other modifications to the compound/ligand including: (a) adding branches to a linear connector; (b) replacing at least one flexible portion of the connector with a rigid group; (c) constraining parts of the connector by cyclization; (d) replacing at least one atom of the connector with atoms or groups of different nature (e.g. carbon to oxygen replacement, oxygen to carbon replacement, etc.); (e) adding or removing atoms or groups to or from the connector to lengthen or shorten the connector, respectively; and (f) adding, removing, or changing groups within at least one of the warheads.

The modification of the tripartite or bifunctional compound/ligand is performed to find a tripartite or bifunctional compound/ligand with increased potency, improved physicochemical properties, and/or improved metabolic stability. The modifications are guided by the trimer conformation such that the trimer complex is stabilized or at least not destabilized too much to lose the corresponding potency. In an embodiment, the length of a modified connector allows the placement of the warheads WA and WB into the respective binding sites of protein A and protein B without change of binding modes. In another embodiment, the selected tripartite or bifunctional compound/ligand that has enhanced ability to induce protein-protein interactions or other cross-domain interactions relative to a parent tripartite or bifunctional compound comprises at least one of: (a) a more rigid connector than the parent compound that adopts the same conformation as the parent in its ternary conformation, (b) fills more hydrophobic cavities than the parent compound in the ternary conformation; and (c) forms additional hydrogen bonds or ion-pair interactions than the parent compound in the ternary conformation.

In an additional embodiment, a modification is considered as a good/favorable modification when the ternary conformation is maintained relative to the parent compound. In another embodiment, a modification is considered a favorable/good modification when a surface area burial for ternary conformation for the modified compound is about equal to or greater than that of the parent compound. Conversely, a decrease in burial surface relative to a parent compound indicates that the modification was unfavorable or bad.

The modified compounds that are judged reasonable by the modeling studies above are synthesized and tested with the assay methods described in the previous section. If one seeks to optimize the physicochemical properties or metabolic stability, the corresponding parameters for the compound are measured also. Several cycles of modeling, modification, synthesis and testing may be needed to achieve the desired objectives of optimization.

In an embodiment, the capability of a compound to induce a protein-protein interaction is determined through biochemical experiments in which the ternary $IC_{50}$ and binary $IC_{50}$s are measured in an aqueous solution or buffer containing related proteins and compound. In another embodiment, the capability of a compound to induce a protein-protein interaction is determined through cell-based assays in which a compound is added to a medium containing a cell line expressing the related proteins. The related proteins can be intracellular proteins or membrane-bound proteins. The ternary and binary $IC_{50}$s are the total compound concentrations in the respective conditions. In a particular embodiment, the $IC_{50}$s are determined by measuring specific cellular responses reflective of, and proportional to, the concentrations of the corresponding ternary species and binary species formed by the added compound with the corresponding proteins. In another embodiment, the binary $IC_{50}$s is determined by using decoy compounds wherein one of the warheads is altered in a way that its binding to the corresponding target is disabled. Comparing a ternary binding $IC_{50}$ and the corresponding binary binding $IC_{50}$s can provide a measurement of the protein-protein interaction. In a cell-based assay, the individual $IC_{50}$s are affected by the membrane permeability of the compound, however, the ratio between the ternary binding $IC_{50}$ and the corresponding binary binding $IC_{50}$s is independent of the membrane permeability because the factor of the membrane permeability is canceled out.

In another embodiment, the chemical matter of the present disclosure (i.e., the ligand) can be administered to animals for in vivo experiments. After administration, the pharmacokinetic parameters of the compound can be measured to examine the effects of the compound in different tissues and blood components. The in vivo functional effects the compound has on, e.g. Tumor Growth Inhibition (TGI), Prostate-Specific Antigens (PSA) as well as others, can be examined/measured.

The composition of the present disclosure may be administered to a subject, e.g., a human, in any medically acceptable way, and which may depend on the disease condition or injury being treated. Possible administration routes include e.g., injections, by parenteral routes such as intravascular, intravenous, intraepidural or others, as well as oral, nasal, ophthalmic, rectal, topical, or pulmonary, e.g. by inhalation. Administration is discussed in greater detail below.

In one embodiment, the method comprises performing molecular dynamics simulations with explicit water and counter-ions on ternary complexes A-L-B with protein A and protein B as target proteins and the ligand L binding to the proteins A and B simultaneously. In an embodiment, the method includes determining the most populated conformation (representative conformation) during a simulation trajectory. In an additional embodiment, the method comprises examining the protein-protein interactions in the simulated structures. As such, the ligand can be redesigned to have a better fit to ternary complexes based on the simulated structures.

In another embodiment, the method comprises determining crystal structures of at least one ternary complex A-L-B with x-ray crystallography or NMR spectroscopy. The protein-protein interactions in the ternary complexes can be examined, and the ligands can be redesigned based on the complex structures. In another embodiment, the method comprises monitoring the protein-protein interactions by detecting spectroscopic signals of the relevant groups of the molecules. In yet another embodiment, the method comprises inferring the protein-protein interactions from heat absorption or release of the ternary binding and binary binding processes using calorimetry-based methods.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure ion may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the disclosure, one or more compounds according to the present disclosure are co-administered with another bioactive agent, such as an erythropoietin stimulating agent or would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure are set forth hereinabove.

The description provides therapeutic compositions as described herein for effectuating the degradation of proteins of interest for the treatment or amelioration of a disease, e.g., cancer. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a ILM and a PTM, preferably linked through a linker moiety, as otherwise described herein, wherein the ILM is coupled to the PTM and wherein the ILM recognizes a ubiquitin pathway protein (e.g., an ubiquitin ligase, preferably an E3 ubiquitin ligase such as, e.g., cereblon) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or emeliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in that patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states of conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by compounds according to the present disclosure include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present disclosure include aceruloplasminemia, Achondrogenesis type II, achondroplasia, Acrocephaly, Gaucher disease type 2, acute intermittent *Porphyria*, Canavan disease, Adenomatous Polyposis Coli, ALA dehydratase deficiency, adenylosuccinate lyase deficiency, Adrenogenital syndrome, Adrenoleukodystrophy, ALA-D *Porphyria*, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic *Porphyria*), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic *Porphyria*, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic *Porphyria*, erythropoietic protoporphyria, erythropoietic uroporphyria, Friedreich's ataxia, familial paroxysmal polyserositis, *Porphyria* cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic *Porphyria*), haemochromatosis, Hallgren syndrome, sickle cell anemia, hemophilia, hepatoerythropoietic *Porphyria* (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic *Porphyria* (variegate *Porphyria*), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymüller syndrome, Wolf-Hirschhorn syndrome, Wolff Periodic disease, Weissenbacher-Zweymüller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY- 142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC 125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-

3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 342-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

EXAMPLES

Embodiments of the present disclosure generate compounds likely to induce protein-protein interactions inside cells for the following protein pairs: AR with VHL, AR with cereblon, ER with VHL, BRD4 with VHL, and BRD4 with cereblon. Molecular dynamics simulations of the corresponding ternary systems and measurements of compound potencies in the related cell-based assays, as exemplified by the embodiments below, were performed and led to the surprising and unexpected discovery of the method of the disclosure. The following examples are intended to illustrate but not to limit the disclosure in any manner, shape or form, either explicitly or implicitly. While they are typical of those that might be used, other procedures, methodologies, or techniques known to those skilled in the art may alternatively be used.

Examination of Tripartite Ligand AR-C-VHL.

A tripartite ligand L with the following structure was examined:

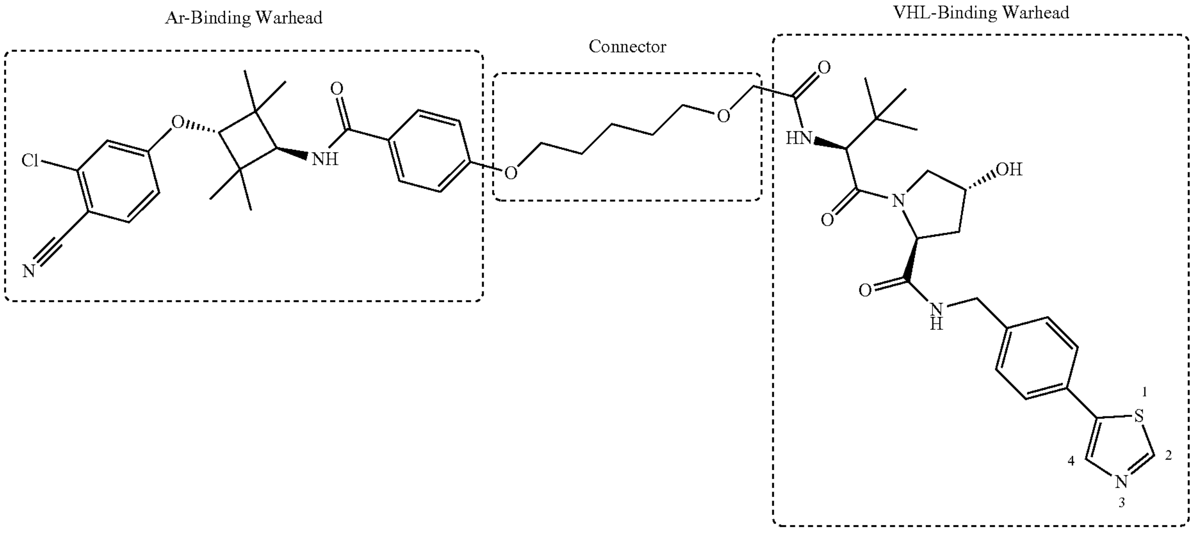 [SMILES: CC(C)(C)[C@H](NC(=O)COCCCCCOc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2cncs2)cc1]

It is composed of an AR-binding warhead which is connected to a VHL-binding warhead by a linear connector. This compound was incubated with VCaP cells which have significant expression of AR and VHL E3 ligase system. The experimental outcome indicated that the compound caused AR degradation with an $IC_{50}$ of 0.688 nM. The compound's (i.e., the ligand's) potency was much greater than the estimated binary binding potencies. The binary binding potency of the ligand L to AR was 342 nM based on a separate cell-based assay measuring displacement of a known AR ligand R1881 by the compound. The binary binding potency of the ligand L to VHL was estimated to be weaker than 3960 nM in the cells because the corresponding $IC_{50}$ in a biochemical binding assay was 3960 nM and the membrane permeability of the compound was shown to be very low. The ratio between the smaller binary binding $IC_{50}$s and the ternary binding $IC_{50}$ was about 497-fold. MD simulation of a ternary system composed of AR ligand-binding domain, a ligand and the complex of VHL with elongin B (EB) and elongin C (EC) in the presence of explicit water was performed. The ligand in the simulation is a close analog of the ligand L above and only differs from the ligand L above by having a methyl substitution at the 4-position of the thiazole group. The simulation led to a dynamic trajectory with substantial protein-protein interactions. The protein-protein interactions add extra binding energy on top of the amounts that stem from the ligand warheads in binding to the respective targets, and thus contribute to the superior/enhanced protein degradation potency relative to the binary binding potencies. This example reveals a way to induce protein-protein interactions via a tripartite or bi-functional ligand and achieve superior or enhanced binding potency and therefore, protein degradation.

Figure 3:
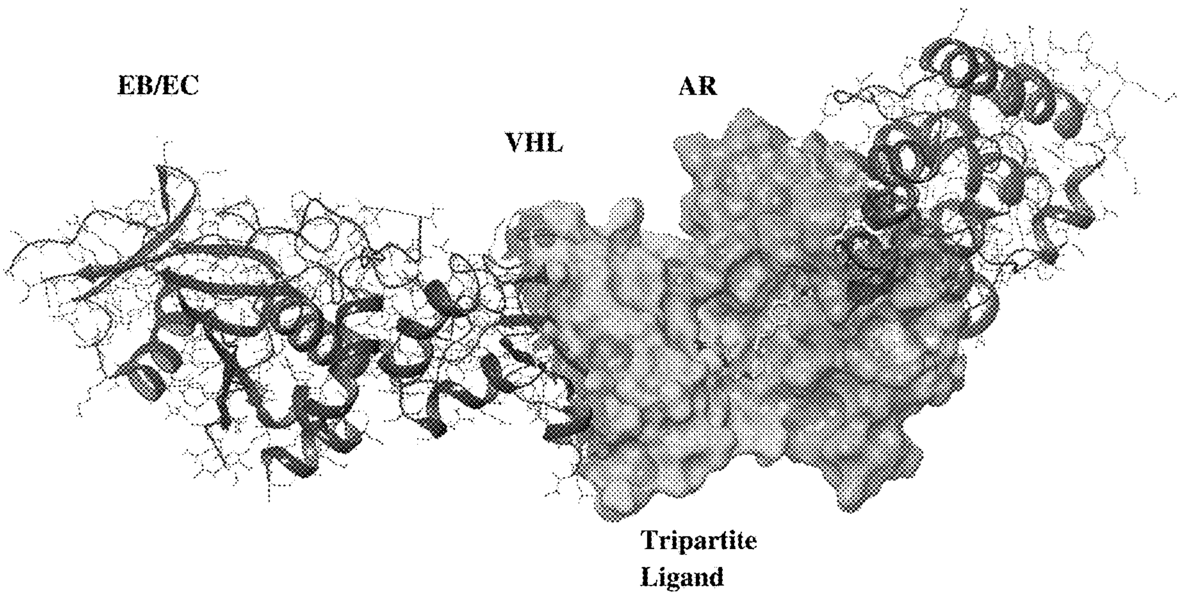
FIG. 3 is an overview of the representative conformation of the AR·L·VHL ternary complex derived from a MD simulation. Elongins B (EB) and Elongins C (EC) are included as part of VHL in the simulation. AR is rendered as purple ribbons and wires; VHL/EB/EC is rendered as dark green ribbons and wires; and the ligand is rendered as tubes with yellow-green color for carbon, red for oxygen and blue for nitrogen. The protein atoms within 10 Å radius of the ligand are covered with molecular surface in which the AR part is in pink and the VHL part is in grey-blue. One can see that the molecular surfaces of AR and VHL merge into a contiguous surface and form a collective binding site for the ligand.
Figure 4:
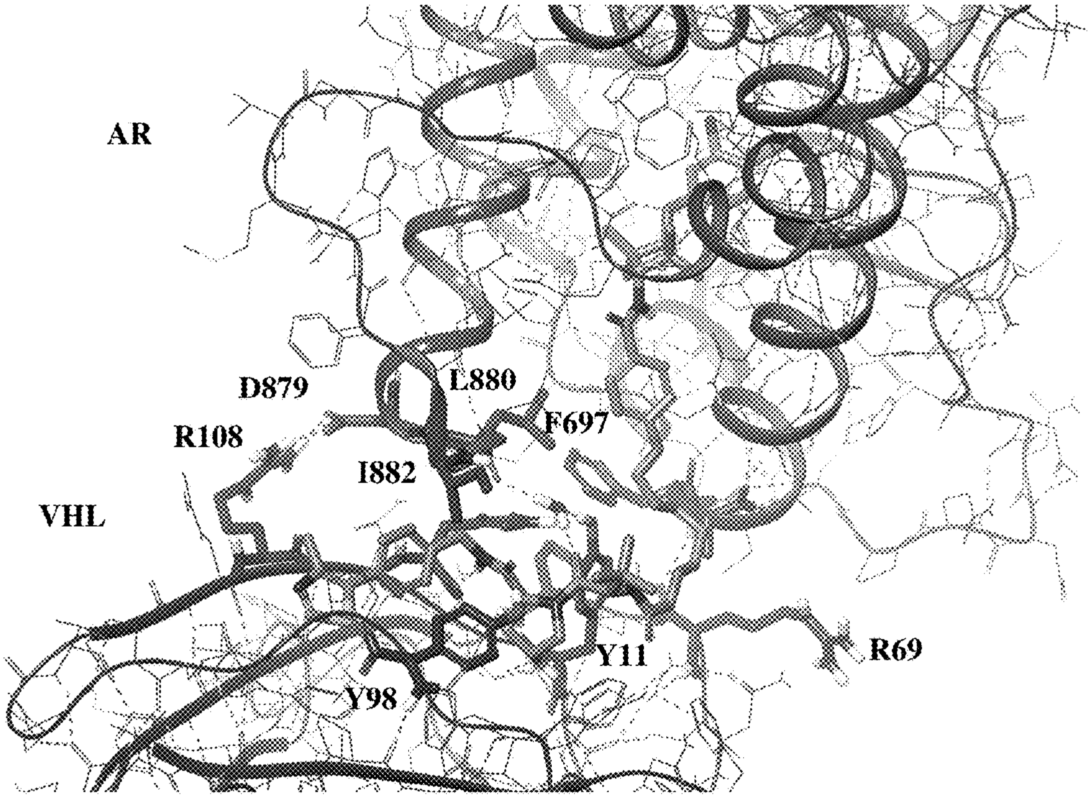
FIG. 4 is an amplified view of the AR·L·VHL ternary complex focused on the ligand and the protein-protein interface. The ligand is represented as tubes with orange for carbon, red for oxygen and blue for nitrogen. AR is in purple ribbons and wires, and VHL is in dark green ribbons and wires. Some of the interfacial residues are in tubes.

The representative conformation derived from the MD simulation of the ternary complex of the AR ligand-binding domain, the ligand and the complex of VHL with EB and EC revealed that the molecular surface of AR merged with that of VHL so that the two proteins formed a collective binding site for the ligand. See FIG. 3. Such a ligand-induced trimer formation of AR·L·VHL caused a large portion of the surface area, i.e. 1716.4 $Å^2$, to be buried relative to the monomeric state, while the formation of a binary complex of AR·L buried a surface area of about 694.7 $Å^2$ and the formation of a binary complex of VHL·L buried a surface area of about 547 $Å^2$. The amount of the surface area buried due to the trimer AR·L·VHL was more than the combined amounts of the surface area buried due to the separate dimers AR·L and L·VHL by about 474.7 $Å^2$. The complex of VHL, EB and EC is considered as one entity and collectively called "VHL" in the descriptions concerning MD simulation in this and other examples. The cross-domain interactions stabilizing the trimer complex, shown in FIG. 4, included an ion-pair between Asp879 of AR and Arg108 of VHL, a hydrophobic cluster composed of Phe697, Ala698 and Leu880 of AR with Pro71, His110, Tyr112 and the nonpolar part of Arg69 of VHL, and a second hydrophobic cluster composed of Ile882 of AR, Tyr98 and Pro99 of VHL and the phenyl-thiazole group of the ligand. The C-terminal end of a a-helix of AR docked onto the phenyl-thiazole part of the ligand. In addition, a water molecule formed stable bridging interactions by forming a trifurcating hydrogen bond with the backbone carbonyl of Leu880 of AR, the side chain phenol of Tyr112 of VHL and the backbone carbonyl of the t-butyl glycine of the ligand. The connector of the ligand interacted with both proteins. A hydrogen bond between the backbone amide of Ala698 of AR and the backbone carbonyl of Arg69 of VHL was seen in the representative conformation. However, this hydrogen bond underwent disappearing/reappearing cycles during the dynamics trajectory, which could be defined as a transient hydrogen bond.

Examination of Tripartite Ligand BRD4-C-VHL.

A tripartite ligand L with the following structure was examined:

It is composed of a BRD4-binding warhead which is connected to a VHL-binding warhead by a linear connector. This compound was incubated with 22RV1 cells, which have significant expression of BRD4 and VHL E3 ligase system. Either the inhibition of BRD4 (by binding and blocking the active site of BRD4) or the degradation of BRD4 leads to the down-regulation of the expression level of a downstream protein c-Myc. The experimental outcome in an ELISA assay demonstrated that the compound down-regulated the c-Myc expression with an $IC_{50}$ of 0.305 nM. A Western blot assay confirmed that the degradation potency $DC_{50}$ of this compound with respect to BRD4 was less than 1 nM. A decoy compound which differs from the ligand L above by having inverse chirality at c1 and c2 positions, and thus lack VHL-binding capability, showed an $IC_{50}$ greater than 1000 nM in c-Myc expression. Since the decoy compound has no VHL-binding capability while retaining the BRD4-binding capability, the effect produced by the decoy compound should be attributed to the binary binding to BRD4. Therefore, it can be inferred that the binary binding potency of ligand L to BRD4 is greater than 1000 nM. The binary binding potency of the L to VHL was 3960 nM in a biochemical assay suggesting that the corresponding binary $IC_{50}$ in the cell assay should be greater than this value given the poor membrane permeability of this type of compounds. The ratio between the smaller binary binding $IC_{50}$ and the ternary binding $IC_{50}$ is greater than 3279-fold. MD simulation of a ternary system composed of BRD4 bromodomain 1, the ligand L and the complex of VHL with EB and EC in the presence of explicit water was performed. The simulation resulted in a dynamic trajectory with substantial protein-protein interactions. The protein-protein interactions provided extra stabilization energy to the ternary complex, and therefore, contribute to the superior/enhanced protein degradation potency relative to the binary binding potencies. As such, this is another example that a tripartite or bi-functional ligand can induce protein-protein interactions and achieve superior potency (e.g., binding and/or protein degradation).

Figure 5:
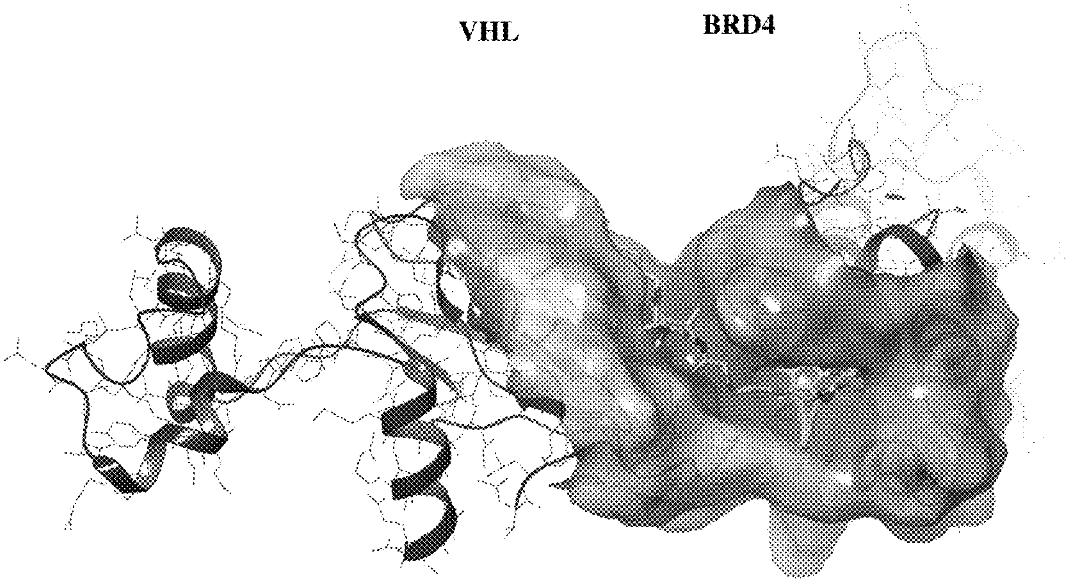
FIG. 5 is an overview of the representative conformation of the BRD4·L'·VHL ternary complex derived from a MD simulation. BRD4 is rendered as purple ribbons and wires; VHL is rendered as dark green ribbons and wires; and the ligand is rendered as tubes with yellow-green color for carbon, red for oxygen and blue for nitrogen. The protein atoms within 10 Å radius of the ligand are covered with molecular surface in which the BRD4 part is in pink and the VHL part is in grey-blue. One can see that the molecular surfaces of BRD4 and VHL merge into a contiguous surface and form a collective binding site for the ligand.

The representative conformation derived from the MD simulation of the ternary complex of the BRD4 bromodomain 1, the ligand L' and VHL revealed that the molecular surface of BRD4 merged with that of VHL so that the two proteins formed a collective binding site for the ligand. (Ligand L' differs from Ligand L by not having a methyl group on the benzylic position of the VHL ligand.) See FIG. 5. Such a ligand-induced trimer formation of BRD4·L'·VHL

Figure 6:
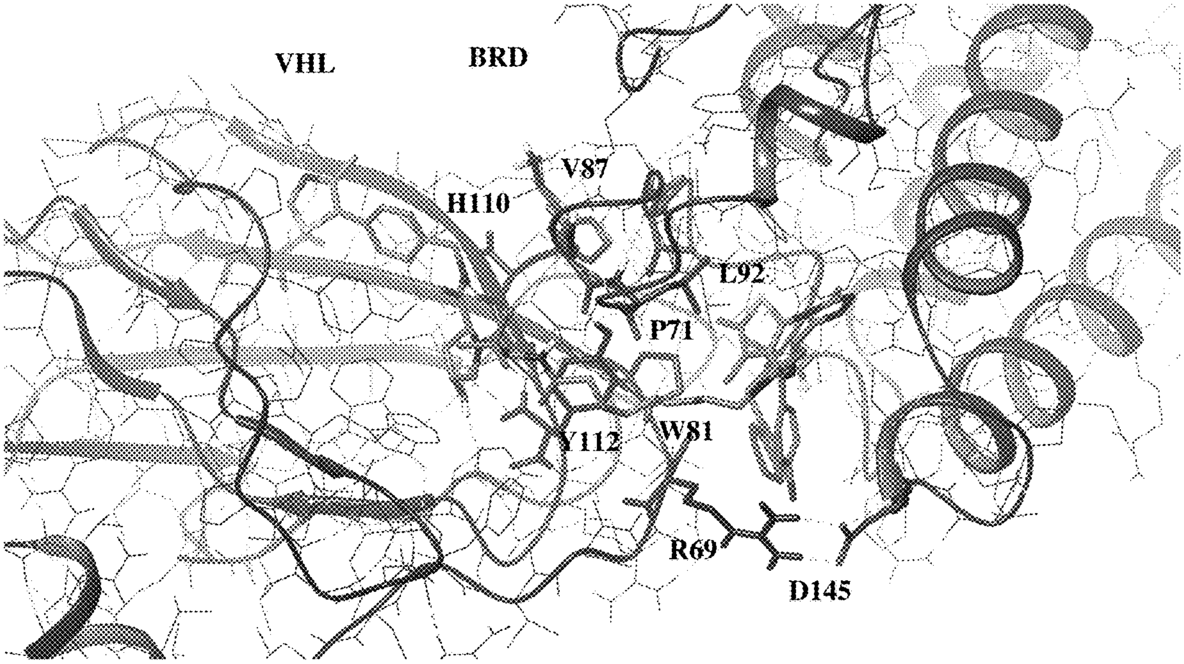
FIG. 6 is an amplified view of the BRD4·L'·VHL ternary complex focused on the ligand and the protein-protein interface. The ligand is represented as tubes with orange for carbon, red for oxygen and blue for nitrogen. BRD4 is in purple ribbons and wires and VHL is in dark green ribbons and wires. Some of the interfacial residues are in tubes.

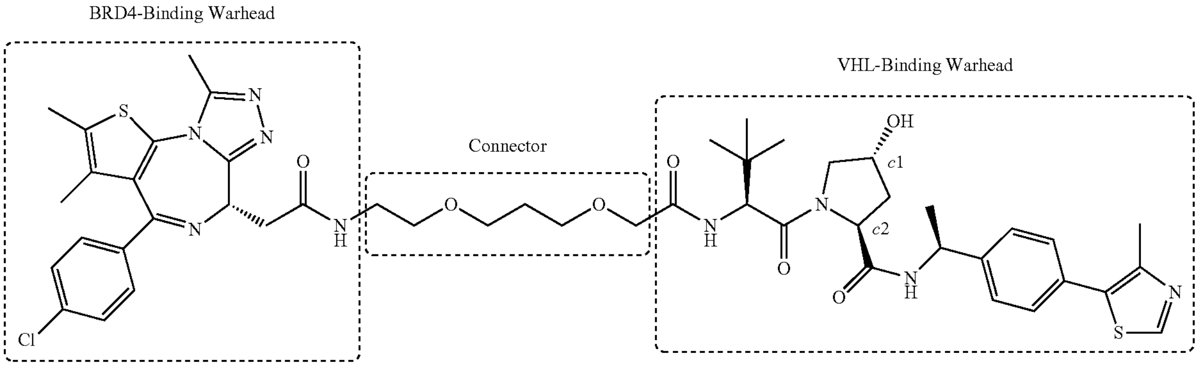 [SMILES: Cc1ncsc1-c1ccc([C@H](C)NC(=O)[C@@H]2C[C@@H](O)CN2C(=O)[C@@H](NC(=O)COCCCOCCNC(=O)C[C@@H]2N=C(c3ccc(Cl)cc3)c3c(sc(C)c3C)-n3c(C)nnc32)C(C)(C)C)cc1]

caused a large portion of the surface area to be buried, i.e. about 1760.9 Å$^2$, relative to the monomeric state, while the formation of a binary complex of BRD4·L' buried a surface area of about 572.4 Å$^2$ and the formation of a binary complex of VHL·L' buried a surface area of about 660 Å$^2$. The amount of the surface area buried due to the trimer BRD4·L'·VHL was more than the combined amounts of the surface area buried due to the separate dimers BRD4·L' and L'·VHL by about 528.5 Å$^2$. The cross-domain interactions stabilizing the trimer complex (FIG. 6) included a hydrophobic cluster contributed by Trp81, Val87, Leu92 and the dimethylthienyl part of the BRD4-binding warhead from the BRD4 side and Pro71, Tyr112 and His110 of VHL, and an ion-pair interaction between Asp145 of BRD4 and Arg69 of VHL. The cross-domain interactions also included the contributions from the connector which interacted with both BRD4 and VHL.

Examination of the Length n of the Connector Linking an AR-Binding Warhead and a VHL-Binding Warhead.

Figure 7:
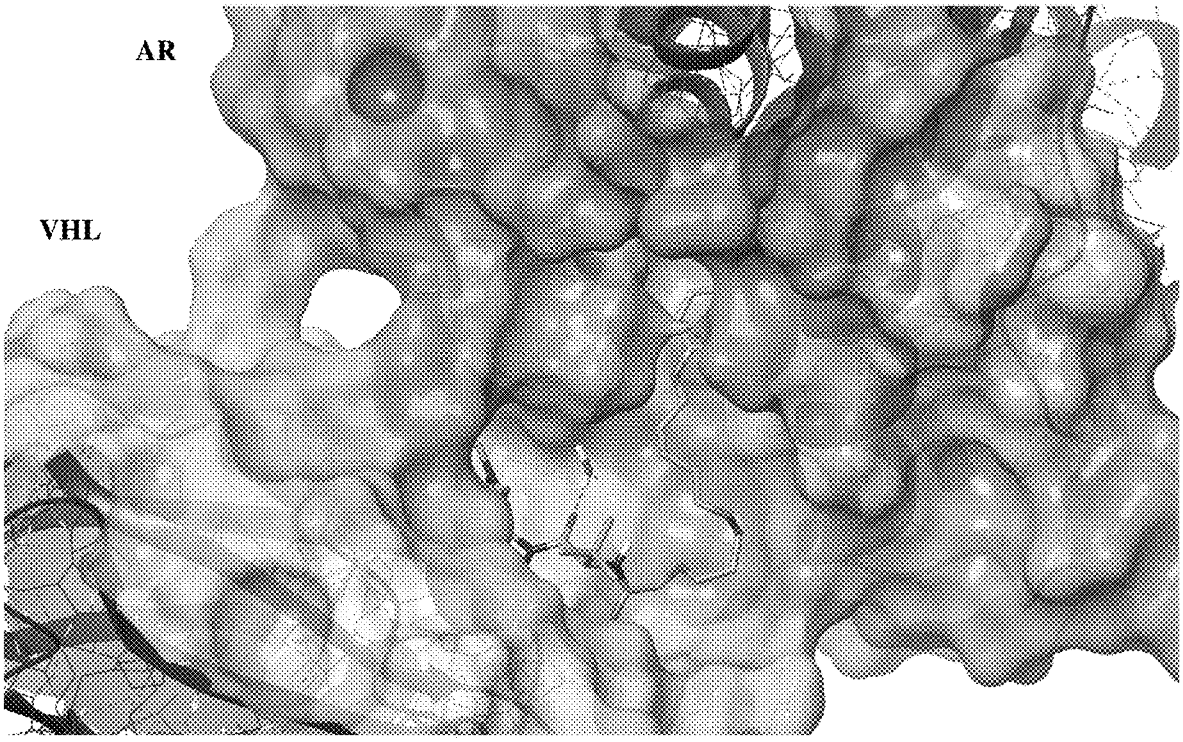
FIG. 7 visualizes the trimer of AR, VHL and a tripartite ligand where AR and VHL dock together, and the ligand connector interacts with the proteins while allowing the warheads to plug into the respective binding sites. This suggests that the length and the chemical composition of the connector are important for the potency of the compound.

The connector linking the AR-binding warhead and the VHL-binding warhead was systematically probed from 4 to 23 atoms. The results are shown in Table 1. The AR degradation potency $DC_{50}$ and the maximum percentage of degradation $D_{max}$ of AR in LNCaP cells were measured for each of these compounds. While $DC_{50}$ is the primary measure of the degradation potency, $D_{max}$ provides a second measure in that a compound is considered to be weak if its $D_{max}$ is not sufficiently high (<60%) with respect to its $DC_{50}$. The binary binding potency with respect to AR was also measured for some of the compounds by the cell-based ligand (R1881) displacement assay. The ratio α between the AR-binding potency and the degradation potency are calculated when it is possible. The results demonstrate that when n ranges between 11 and 14 atom, the degradation potency reaches the optimum and exhibits a superior binding/degradation potency over the binary binding potencies. When n is gradually shortened from 11 atoms, the degradation potency declines until 8 atoms, where degradation potency drops off. These results are consistent with the notion of a stable trimer in which the connector needs to be sufficiently long to span a defined distance. Otherwise, clashes between the proteins or dislocation of the warhead(s) are expected. When n is larger than the optimum range, the degradation potency also decreased. Ligands with a larger n required that one protein molecule to explore a larger volume of space translationally and rotationally with respect to another protein molecule in order to find the specific interaction surface(s), and as a result, the formation of a protein-protein interaction complex is more difficult due to the entropic effect. MD simulation on compounds 8 and 9 showed that these compounds induced similar trimer complexes (complexes with protein-protein interactions). The representative conformation of the trimer for compound 9 is shown in FIG. 7, indicating that a connector of a length of 12 atoms is compatible with the trimer conformation. The connector adopts a near-extended conformation with few twists, consistent with the fact that shortening the connector to 11 atoms long (compound 8) is well-tolerated, but further shortening starts to destabilize the trimer. The connector is not totally solvent-exposed, but binds to the induced pocket formed by the two protein molecules, suggesting that changing the connector length will change its interaction energy with the protein molecules as well as its conformational energy stemming from the chain twisting, in addition to the entropic effect mentioned above.

AR-Binding Warhead

VHL-Binding Warhead

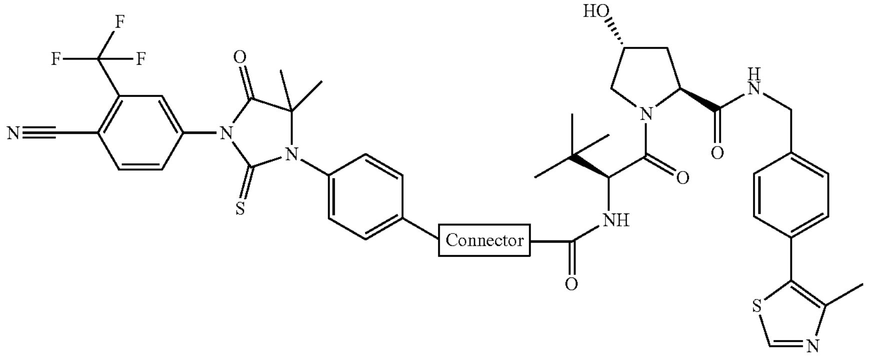

TABLE 1

Exploration of Connector Length n Linking an AR-Binding Warhead and a VHL-Binding Warhead, Measurement of AR Degradation Potency $DC_{50}$, Maximum AR Degradation $D_{max}$, Binary Binding Potency $IC_{50}$ to AR in cells and Calculation of the Ratio α between $DC_{50}$ and $IC_{50}$.

| ID | Connector | n | $DC_{50}$ (μM) | $D_{max}$ (%) | $IC_{50}^{AR}$ (μM) | α |
|---|---|---|---|---|---|---|
| 1 | 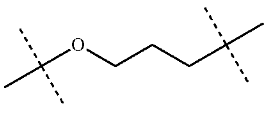 | 4 | >3 | 35 | 0.97 | <1 |

TABLE 1-continued
Exploration of Connector Length n Linking an AR-Binding Warhead and a VHL-Binding Warhead, Measurement of AR Degradation Potency $DC_{50}$, Maximum AR Degradation $D_{max}$, Binary Binding Potency $IC_{50}$ to AR in cells and Calculation of the Ratio α between $DC_{50}$ and $IC_{50}$.
| ID | Connector | n | $DC_{50}$ (μM) | $D_{max}$ (%) | $IC_{50}^{AR}$ (μM) | α |
|---|---|---|---|---|---|---|
| 2 | 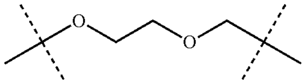 | 5 | 1.7 | 51 | 2.14 | <1 |
| 3 | 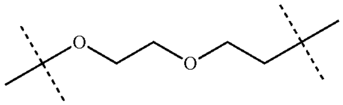 | 6 | 9.3 | 56 | | |
| 4 | 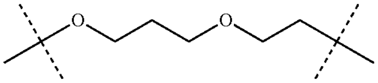 | 7 | >3 | 18 | | |
| 5 | 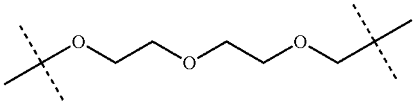 | 8 | >3 | 38 | 2.08 | <1 |
| 6 | 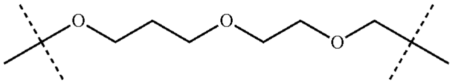 | 9 | 0.072 | 54 | | |
| 7 | 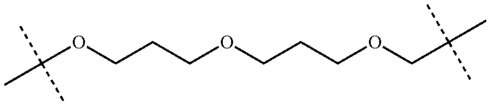 | 10 | 0.39 | 56 | | |
| 8 | 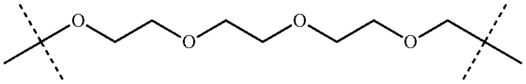 | 11 | 0.0262 | 62 | 2.14 | 81.7 |
| 9 | 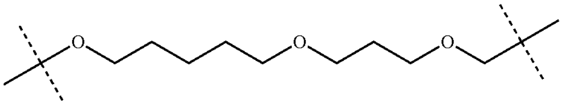 | 12 | 0.0344 | 83 | 0.81 | 23.5 |
| 10 | 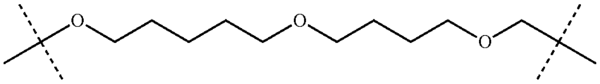 | 13 | 0.060 | 77 | | |
| 11 | 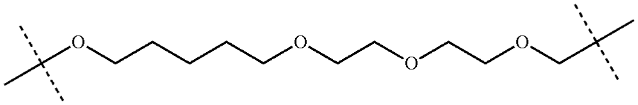 | 14 | 0.011 | 60 | 1.15 | 105 |
| 12 | 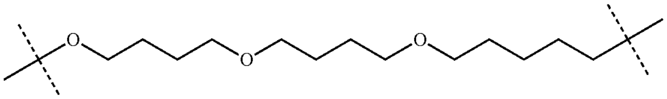 | 16 | >3 | 42 | 1.15 | <1 |
| 13 | 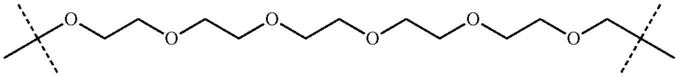 | 17 | >3 | 24 | 5.29 | <1 |
| 14 | 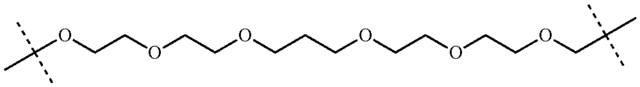 | 18 | 0.22 | 52 | 4.95 | |
| 15 | 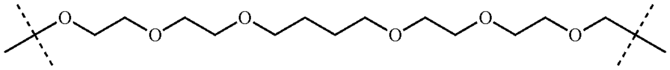 | 19 | 0.029 | 58 | 3.48 | |

TABLE 1-continued

Exploration of Connector Length n Linking an AR-Binding Warhead and a VHL-Binding Warhead, Measurement of AR Degradation Potency $DC_{50}$, Maximum AR Degradation $D_{max}$, Binary Binding Potency $IC_{50}$ to AR in cells and Calculation of the Ratio α between $DC_{50}$ and $IC_{50}$.

| ID | Connector | n | $DC_{50}$ (μM) | $D_{max}$ (%) | $IC_{50}^{AR}$ (μM) | α |
|---|---|---|---|---|---|---|
| 16 | 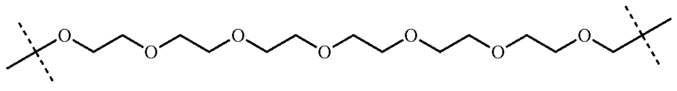 | 20 | 3.0 | 90 | 1.75 | 0.58 |
| 17 | 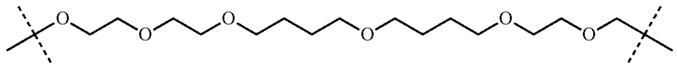 | 21 | >3 | 43 | 1.42 | <1 |
| 18 | 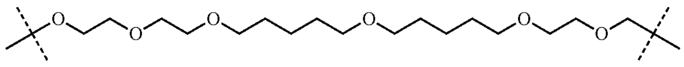 | 23 | >3 | 47 | 0.96 | <1 |

Examination of the Length n of the Connector Linking a BRD4-Binding Warhead and a Cereblon-Binding Warhead.

Figure 8:
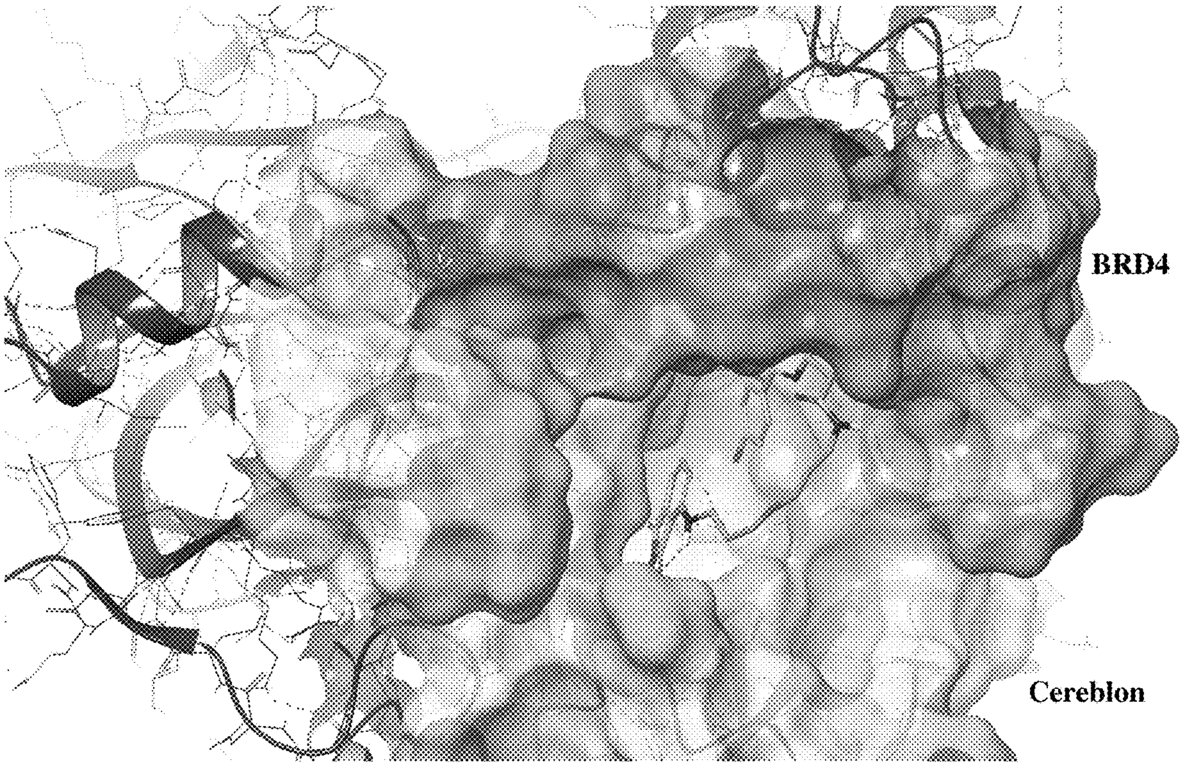
FIG. 8 visualizes the trimer of BRD4, cereblon and a tripartite ligand where BRD4 and cereblon dock together, and the ligand connector adopts a conformation to allow the warheads to dock into the respective binding sites and also dock against each other at the same time. This further suggests that both the length and the chemical composition of the connector are important for the potency of the compound.

The connector linking the BRD-4 binding warhead and the cereblon-binding warhead was systematically probed from 2 to 8 atoms. The data is shown in Table 2. For comparison, the parent inhibitor of BRD4 (compound JQ1) was also prepared. Each compound was incubated with 22RV1 cells which have significant expression of BRD4 and the cereblon E3 ligase system. The expression level of a downstream protein c-Myc was measured. In this assay, either the inhibition of BRD4 (by binding and blocking the active site of BRD4) or the degradation of BRD4 leads to the down-regulation of the expression level of c-Myc. The results indicated that a connector length of 5 or 7 atoms led to the most potent $IC_{50}$ (0.682 or 0.049 nM). Shortening the length to 4 atoms or less decreases the compound potency to a stationary level around 120 to 250 nM, while extending the length to 8 atoms decreases the compound potency to about 13 nM. The BRD4 inhibitor JQ1 exhibited an $IC_{50}$ of 101 nM, similar to those with shorter connectors. It is likely that the compounds with connector lengths less than 5 atoms act like pure BRD4 inhibitors, which bind and inhibit BRD4 without causing degradation. The c-Myc expression inhibition $IC_{50}$ of these compounds reflect the binary binding potency to BRD4. The compounds with greater connector lengths induce ternary complex formation which recruits BRD4 and cereblon together and causes ubiquitination of BRD4 by the cereblon E3 ligase system and the subsequent degradation of BRD4. The degradation potencies substantially surpass the binary inhibitory potency due to the binding to BRD4. They also surpass the binary binding potency of the cereblon-binding warhead (pomalidomide), since pomalidomide has a $K_d$ of 157 nM based on the literature (Fischer et al. *Nature* 2014). The MD simulations on compounds 23 and 24 showed that these compounds induced similar trimer complexes in which cereblon directly interacted with the bromodomain 1 of BRD4. The representative conformation of the trimer for compound 24 is given in FIG. 8, and which demonstrates that a connector length of 7 atoms is compatible with the trimer conformation. The connector lengths shorter than 5 atoms are too short to span the distance required to allow the predicted trimer, consistent with the observed lower potencies. The difference in potency between compound 22 and compound 23, which differ by having an oxygen-to-carbon replacement in the middle of the connector, can be rationalized by the fact that the oxygen atom facilitates the gauche conformation of the next adjacent bond. In addition to the interactions between BRD4 and cereblon, the BRD4-binding warhead and the cereblon-binding warhead also interact between each other. These cross-domain interactions largely contribute to the stability of the ternary complexes, and thus to the potency of the corresponding compounds.

BRD4-Binding Warhead Cereblon-Binding Warhead

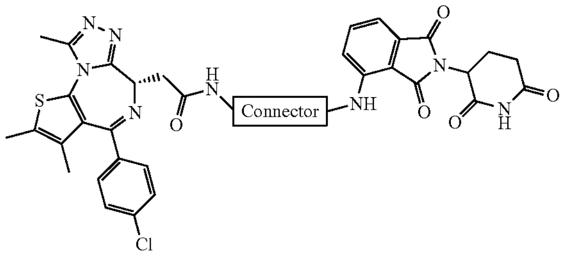

JQ1

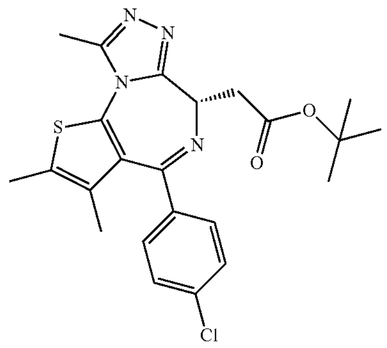

TABLE 2

Exploration of Connector Length n Linking a BRD4-Binding Warhead and a Cereblon-Binding Warhead and Measurement of c-Myc Expression Inhibition $IC_{50}$ and Maximum Inhibition $I_{max}$ in 22RV1 cells.

| ID | Connector | n | $IC_{50}$ (μM) | $I_{max}$ (%) |
|---|---|---|---|---|
| 19 | 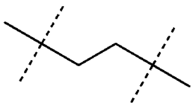 | 2 | 0.187 | 96 |
| 20 | 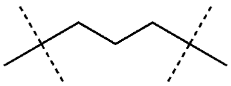 | 3 | 0.123 | 93 |
| 21 | 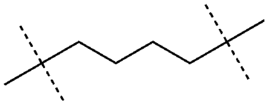 | 4 | 0.250 | 88 |
| 22 | 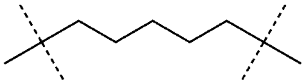 | 5 | 0.00379 | 100 |
| 23 | 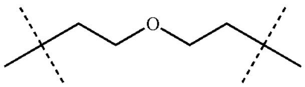 | 5 | 0.000682 | 100 |
| 24 | 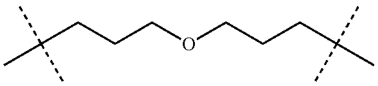 | 7 | 0.000049 | 98 |
| 25 | 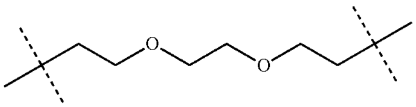 | 8 | 0.013 | 100 |
| JQ1 | | | 0.101 | 93 |

Examination of the Length n of the Connector Linking a BRD4-Binding Warhead and a VHL-Binding Warhead.

Figure 9:
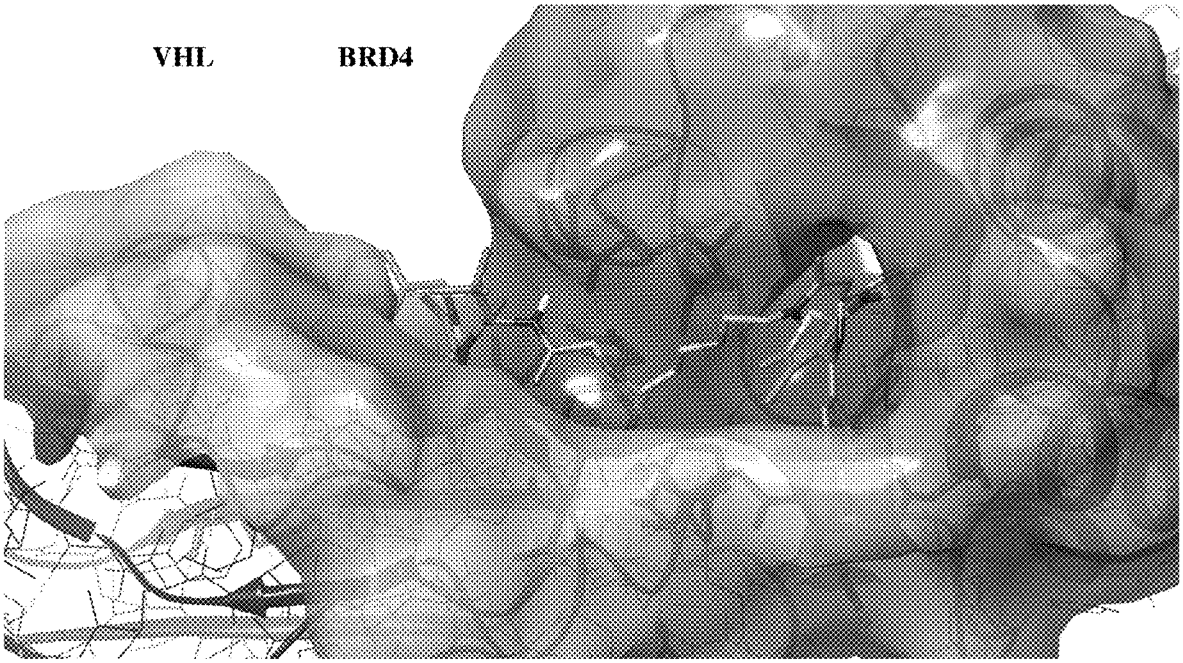
FIG. 9 visualizes the trimer of BRD4, VHL and the most potent ligand from the connector length exploration. BRD4 is covered by pink surface. VHL is covered by grey-blue surface. The ligand is rendered as tubes with the warheads' carbon atoms in orange and the connector's carbon atoms in yellow-green.

The connector linking the BRD4 warhead and the VHL-binding warhead was systematically probed from 5 to 19 atoms. The results are shown in Table 3. Each compound was incubated with 22RV1 cells which have significant expression of BRD4 and the VHL E3 ligase system. The expression level of a downstream protein c-Myc was measured. In this assay, either the inhibition of BRD4 (e.g., by binding and blocking the active site of BRD4) or the degradation of BRD4 results in the down-regulation of the expression level of c-Myc. The results indicate that the connector length range between 8 and 11 atoms gave rise to the optimal range of $IC_{50}$ (0.16 to 19 nM). Shortening the length of the connector to 5-7 atoms decreased the compound potency to a stationary level around 78 to 95 nM. Extending the length of the connector from 11 to 19 atoms gradually decreased the compound potency to about 700 nM. The degradation potencies corresponding to the optimal connector length range substantially surpass the binary inhibitory potencies due to the binding to BRD4 or VHL. The MD simulations on compound 29 showed that this compound induced a trimer in which VHL directly interacted with the bromodomain 1 of BRD4. The representative conformation of the trimer is shown in FIG. 9, indicating that a connector length of 8 atoms is compatible with the trimer conformation. The connector lengths of 5 to 7 atoms disturb the trimer conformation, consistent with the observed lower potencies. Extending the connector length longer than 8 atoms is tolerated because the connector in this case is significantly exposed to solvent. A longer connector can adopt a loop conformation with the middle part projecting to the solvent space. However, long connectors will suffer entropic penalties as previously stated.

In order to study the roles of the oxygen atoms in the connector of compound 29, these oxygen atoms were replaced by carbon atoms, sulfur atom or sulfonic group. The results are shown in Table 4. It turned out that the oxygen atom closer to the BRD4 side was important for the potency while the other oxygen atom seems important in a lesser extent. As shown in FIG. 9, the predicted trimer conformation showed the first oxygen atom facilitated the gauche conformation between this atom and the amide group. Replacing it with a carbon atom, a sulfur atom or a sulfonic group destabilizes the conformation and thus leads to the decrease of potency. The sulfonic group would be particularly disturbing due to the conformational restraints and desolvation cost. These results demonstrate that although the length is the primary requirement for a connector to allow trimer formation, the chemical composition of the connector is also important since the connector needs to adopt specific conformations in certain regions and it has certain interactions with the targets.

Demonstration of the Induction of the Protein-Protein Interactions Between VHL and ER-α by Two Tripartite Compounds Using Surface Plasmon Resonance (SPR) Method.

The SPR experiments were conducted on a Biacore3000 (GE Healthcare). His-tagged VHL protein was immobilized on a carboxymethylated dextran surface with nitriloacetic acid, taking advantage of NTA/$Ni^{2+}$ chelation. The dissociation constant ($K_d$) of a compound to VHL was determined in a twelve point-concentration assay, and the $K_d$ of the equimolar mixture of a same compound and ER-α to VHL was determined in a same way, which allows the comparison of the two $K_d$ values. This comparative experiment was done for two tripartite compounds respectively. Each of the two tripartite compounds contains an ER-binding warhead and a VHL-binding warhead with a connector covalently linking the two warheads. The two compounds only differ in their ER-binding warheads. This set of experiments indicated that the $K_d$ of the first compound to VHL in the absence of ER-α was about 1.00 μM while the $K_d$ to VHL was changed to 0.010 μM in the presence of ER-α, corresponding to a potency increase of about 100-fold. Similarly, the $K_d$ of the second compound to VHL in the absence of ER-α was about 0.700 μM while the $K_d$ to VHL was changed to 0.0045 μM in the presence of ER-α, corresponding to a potency increase of about 140-fold. These large increases in potency show that the designed tripartite compounds induce the protein-protein interactions and/or cross-domain interactions for the corresponding proteins.

Demonstration of the Induction of the Protein-Protein Interactions Between VHL and ER-α by a Tripartite Compound Using AlphaLisa Assay.

The AlphaLisa assay was performed with GST-ER-α, VHL-His and a tripartite compound composed of an ER-binding warhead and a VHL-binding warhead and a connector. After a ten-minute pre-incubation of the compound with equimolar mixture of GST-ER-α and VHL-His, 7.5 μL of anti-His conjugated AlphaLISA acceptor beads diluted 100× in Buffer A was added to each well of the assay plate, followed by another 5 minute incubation in the dark. Finally, 7.5 μL of glutathione-conjugated AlphaLISA Donor beads diluted 100× in Buffer B was added, followed by another 5 minute incubation at room temperature in the dark. A series of concentrations of the compounds was tested. The percentage of the ternary complex formation at each concentration was calculated from the signal and the dissociation constant $K_d$ of the ternary complex formation was determined. It indicated a $K_d$ of 1.5 nM for the ternary complex formation to compare with the binary binding constant of 209 nM between the compound and ER-α and the binary binding constant of 228 nM between the compound and VHL. Thus, the ternary binding affinity was about at least 139-fold more potent than the binary binding affinities, suggesting that the designed tripartite compound induced the protein-protein interactions for the corresponding proteins. (The binary binding constant between ER-α and the compound was determined using fluorescent polarization assay and the binary binding constant between VHL and the compound was determined using AlphaLisa assay.)

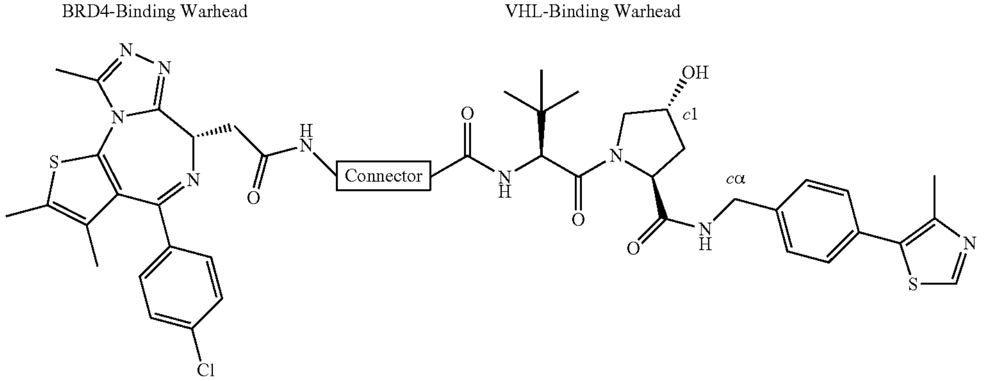

TABLE 3

| Exploration of Connector Length n Linking a BRD4-Binding Warhead and a VHL-Binding Warhead and Measurement of c-Myc Expression Inhibition $IC_{50}$ and Maximum Inhibition $I_{max}$ in 22RV1 cells. | | | | |
|---|---|---|---|---|
| ID | Connector | n | $IC_{50}$ (μM) | $I_{max}$ (%) |
| 26 | 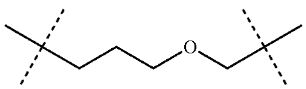 | 5 | 0.095 | 98 |
| 27 | 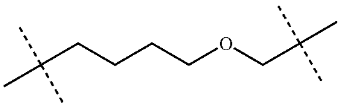 | 6 | 0.078 | 100 |

TABLE 3-continued

Exploration of Connector Length n Linking a BRD4-Binding Warhead and a VHL-Binding Warhead and Measurement of c-Myc Expression Inhibition $IC_{50}$ and Maximum Inhibition $I_{max}$ in 22RV1 cells.

| ID | Connector | n | $IC_{50}$ (μM) | $I_{max}$ (%) |
|---|---|---|---|---|
| 28 | 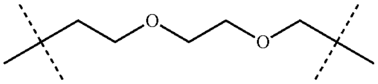 | 7 | 0.0805 | 94 |
| 29 | 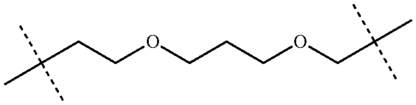 | 8 | 0.00016 | 97 |
| 30 | 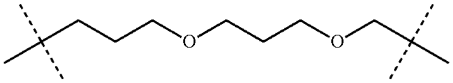 | 9 | 0.0194 | 100 |
| 31 | 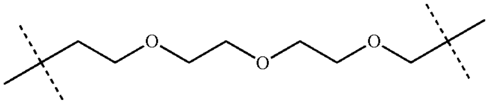 | 10 | 0.00122 | 99.3 |
| 32 | 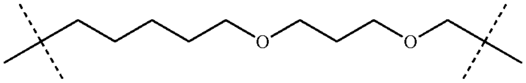 | 11 | 0.00086 | 98 |
| 33 | 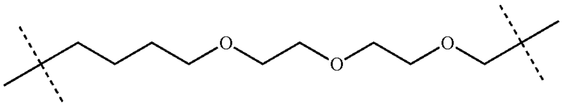 | 12 | 0.005 | 97 |
| 34 | 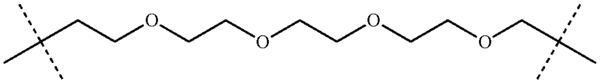 | 13 | 0.034 | 94 |
| 35 | 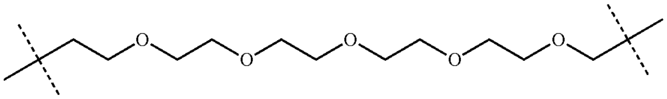 | 16 | 0.206 | 93 |
| 36 | 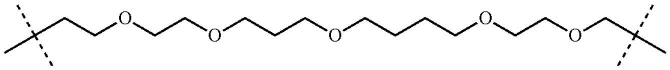 | 17 | 0.126 | 96 |
| 37 | 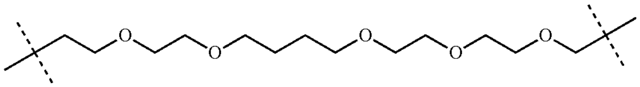 | 18 | 0.202 | 96.4 |
| 38 | 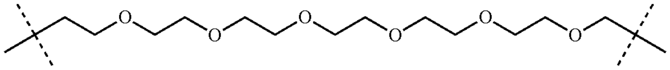 | 19 | 0.707 | 62.2 |

TABLE 4

Changes of Chemical Composition of the Best Connector from the Set in Table 3 and Measurement of c-Myc Expression Inhibition $IC_{50}$ and Maximum Inhibition $I_{max}$ in 22RV1 cells.

| ID | Connector | n | $IC_{50}$ (μM) | $I_{max}$ (%) |
|---|---|---|---|---|
| 29 | 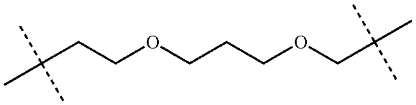 | 8 | 0.00016 | 97 |

TABLE 4-continued

Changes of Chemical Composition of the Best Connector from the Set in Table 3 and Measurement of c-Myc Expression Inhibition $IC_{50}$ and Maximum Inhibition $I_{max}$ in 22RV1 cells.

| ID | Connector | n | $IC_{50}$ (μM) | $I_{max}$ (%) |
|---|---|---|---|---|
| 39 | 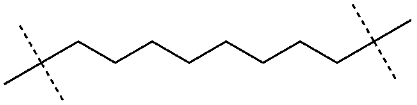 | 8 | 0.0102 | 95.4 |
| 40 | 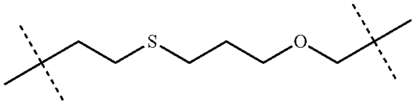 | 8 | 0.0209 | 99 |
| 41 | 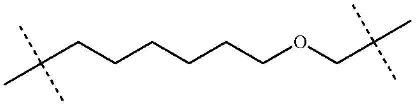 | 8 | 0.0257 | 100 |
| 42 | 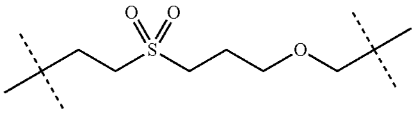 | 8 | 0.122 | 88.3 |

METHODS OF THE EXAMPLES

Molecular Modeling and Molecular Dynamics Simulation.

The computer programs mentioned below are the 2013, 2014 and 2015 releases distributed by Schrodinger Inc. headquartered in New York. The crystal structures of the complexes of VHL/EB/EC with ligands, AR with ligands (PDB codes: 3V4A and 2YLO), BRD4 with ligand (PDB code: 3MXF) and cereblon with ligand (PDB codes: 4TZ4 and 4C12) were retrieved and imported to Maestro98 and Maestro102. The hydrogen atoms and missing side chains were added using Protein Preparation Wizard. For VHL, BRD4 and cereblon complexes, the ligands were modified into the corresponding warheads mentioned in the disclosure. Two crystal structures of cereblon were merged to generate a model of human cereblon. For AR, the crystal structures have the closed conformation concerning H12 helix and adjacent loops which is not compatible with the desired warheads. A homology model of an open conformation was built by combining these crystal structures and the open conformation structures of ER (PDB codes: 1ERR, 3ERT and 2YJA). The H12 helix and the loops of AR were replaced by the corresponding open conformation pieces of ER and the side chains were mutated to the corresponding AR amino acids. The ligand in AR was modified into the desired warheads. Molecular dynamics simulation was performed for each homology model. A representative conformation was generated for each model from the molecular dynamics trajectory. A connector was built to link between each AR-binding or BRD4-binding warhead and each VHL-binding or cereblon-binding warhead while keeping the interactions between each warhead and the corresponding protein counterpart unchanged, using Maestro modeling tools. Each ternary complex obtained in this way was subjected to molecular dynamics simulation and a representative conformation was derived from the trajectory generated.

Each molecular dynamics simulation was done with a general protocol as follows. A system was solvated with explicit water and 0.15 M sodium chloride within a rectangle box of which each face is 10 Å away from the nearest atom of the solute system. The box had such an orientation relative to the solute system that the box volume is minimized. The box was confined using the periodic boundary condition. Additional sodium or chloride ions were added to bring the total charge to zero. The program Desmond was used for simulation with OPLS2.1 force-field. Each simulation underwent seven stages: minimization with restraints on solute, minimization without any restraints, simulation with Berendsen NVT at temperature of 10 K with small time-steps with restraints on solute heavy atoms, simulation with Berendsen NPT at temperature of 10 K with restraints on solute heavy atoms, simulation with Berendsen NPT at temperature of 310 K with restraints on solute heavy atoms, simulation with Berendsen NPT at temperature of 310 K without restraints, and the production stage with RESPA integrator at temperature of 310 K and pressure of 1.01325 bar. The Coulombic interaction was treated with Smooth Particle Mesh Edward method with Ewald tolerance at $1\times e^{-9}$. The energies were saved at every 1.2 picosecond and the trajectory was saved at every 4.8 picosecond. The production stage was typically run for 20 nanoseconds, and when the starting point was a rough model, another 20 nanoseconds follow.

After each molecular dynamics simulation, a cluster analysis was performed on the frames of the last 20 nanosecond trajectory using one of the supporting scripts of Desmond. Different frames were aligned by minimizing the Root-Mean-Square Deviation (RMSD) of the corresponding solute heavy atoms between frames. The RMSD of the aligned frames were used as the distances for clustering using hierarchical method. The entire population of frames was clustered into two clusters. The frame closest to the center of the largest cluster was selected as the representative conformation from the simulation which can be nominally considered as the most populated conformation.

The molecular surface areas were calculated using the Molecular Surface program of Maestro suite with a resolution at 0.3 Å and probe radius of 1.4 Å. The surface burial due to a binary complex formation is defined as the difference between the surface area of the whole binary complex and the sum of the surface areas of the corresponding monomers in isolation. The surface burial due to a ternary complex formation is defined as the difference between the surface area of the whole ternary complex and the sum of the surface areas of the corresponding monomers in isolation. Thus, the surface burials were calculated by first calculating the surface areas of the individual systems and then calculating the differences accordingly.

Chemical Synthesis: General Scheme and Examples.

A tripartite compound of WA-C-WB, or their pharmaceutically acceptable salts, polymorphic forms, prodrugs, solvate forms and isotope containing derivatives thereof, may be prepared by the general approaches described below (scheme 1), together with synthetic methods known in the art of organic chemistry, or modifications and derivatizations that are familiar to those of ordinary skill in the art.

Scheme 1

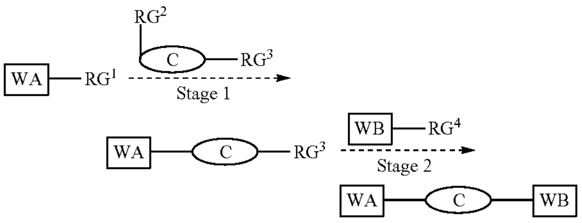

TABLE 5

| Exemplary Compounds. | | |
|---|---|---|
| Ex # | Structure | Compound name and Analytical data |
| E1 | 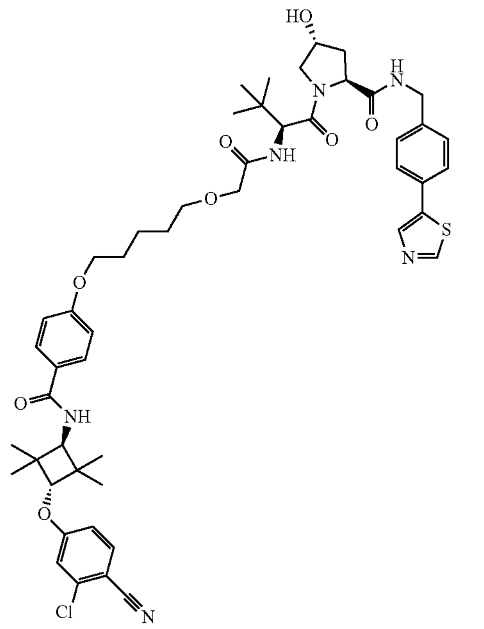 [SMILES: CC(C)(C)[C@H](NC(=O)COCCCCCOc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2cncs2)cc1] | (2S,4R)-1-[(2S)-3,3-dimethyl-2-(2-{[5-(4-{[trans-3-(3-chloro-4-cyanophenoxy)-2,2,4,4-tetramethylcyclobutyl]carbamoyl} phenoxy)pentyl]oxy} acetamido)butanoyl]-4-hydroxy-N-{[4-(1,3-thiazol-5-yl)phenyl]methyl}pyrrolidine-2-carboxamide <br> $^1$H NMR (400 MHz, $CDCl_3$): δ 0.95 (s, 9H), 1.22 (s, 6H), 1.27 (s, 6H), 1.56-1.58 (m, 2H), 1.68-1.70 (m, 2H), 1.83-1.86 (m, 2H), 2.11-2.12 (m, 1H), 2.54 (br, 1H), 3.52-3.63 (m, 3H), 3.91-4.16 (m, 7H), 4.28-4.54 (m, 5H), 4.70-4.71 (m, 1H), 6.19 (d, J = 6.8 Hz, 1H), 6.80-6.97 (m, 4H), 7.17 (d, J = 8.4 Hz, 1H), 7.32 (d, J = 6.8 Hz, 2H), 7.48-7.58 (m, 3H), 7.72-7.74 (m, 2H), 8.03-8.10 (m, 2H), 8.78 (br, 1H); LC-MS: ($ES^+$): m/z 941.20 [M + $H^+$] |
| E2 | 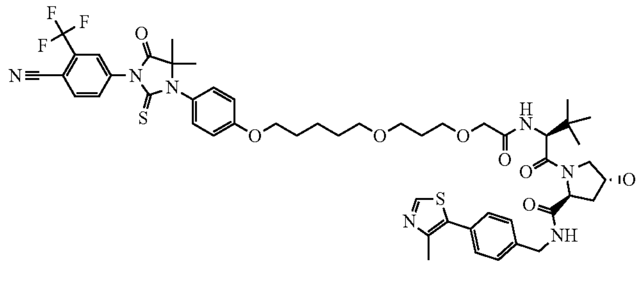 | (2S,4R)-1-((S)-2-(2-(3-(5-(4-(3-(4-cyano-3-(trifluoromethyl)phenyl)-5,5-dimethyl-4-oxo-2-thioxoimidazolidin-1-yl)phenoxy) pentyloxy)propoxy)acetamido)-3,3-dimethylbutanoyl)-4-hydroxy-N-(4-(4-methylthiazol-5-yl)benzyl)pyrrolidine-2-carboxamide <br> 1H NMR (400 MHz, CDC13): δ 7.96 (s, 2H), 7.86 (d, J = 8.6 Hz, 1H), 7.19 (d, J = 8.8 Hz, 2H), 7.02 (d, J = 8.6 Hz, 2H), 4.50 (s, 2H), 4.30 (t, J = 6.4 Hz, 2H), 4.02 (t, J = 6.4 Hz, 2H), 3.53 (m, 2H), 3.44 (m, 2H), 1.96-1.80 (m, 4H), 1.69-1.53 (m, 2H), 1.49 (s, 6H), 1.48 (s, 9H), 1.44-1.22 (m, 2H); Mass (ES+): m/z 686.35 [MNa+] |

Synthesis of Example E1
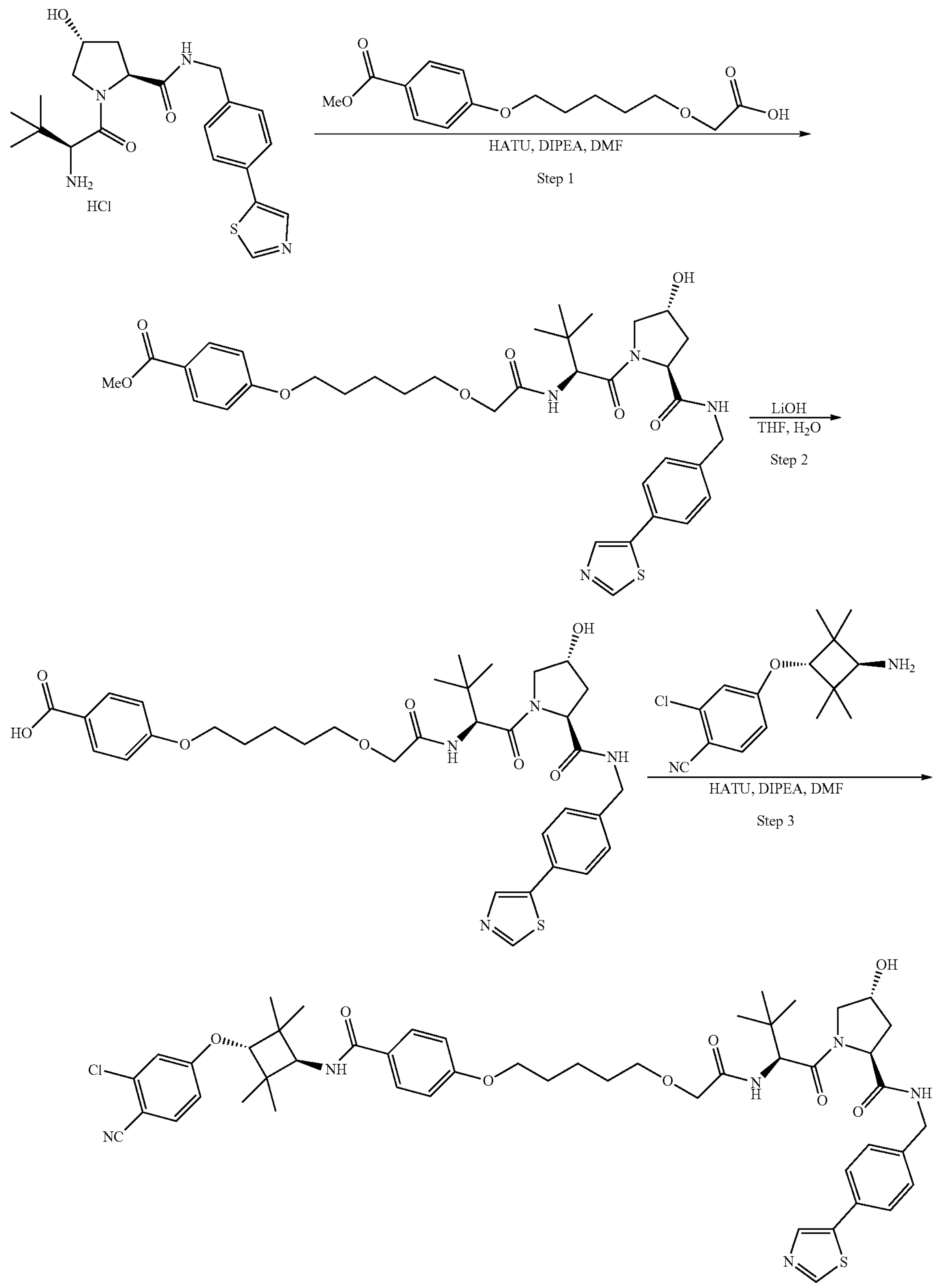
E1

Step 1: Synthesis of methyl 4-{[5-({[(2S)-1-[(2S,4R)-4-hydroxy-2-({[4-(1,3-thiazol-5-yl)phenyl]methyl}carbamoyl)pyrrolidin-1-yl]-3,3-dimethyl-1-oxobutan-2-yl]carbamoyl}methoxy)pentyl]oxy}benzoate

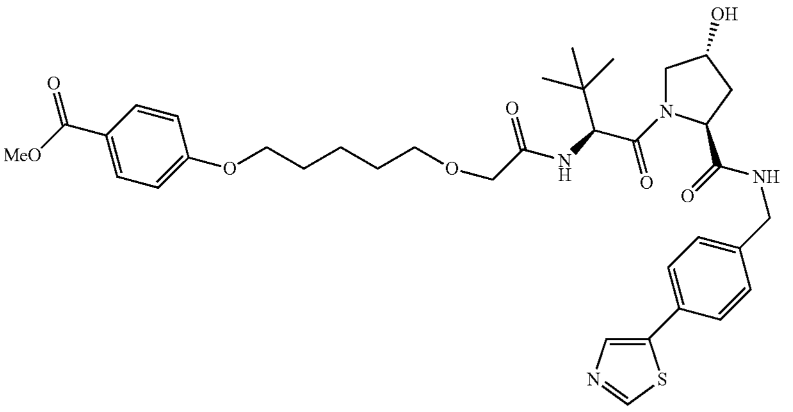 [SMILES: COC(=O)c1ccc(OCCCCCOCC(=O)N[C@H](C(=O)N2C[C@H](O)C[C@H]2C(=O)NCc2ccc(-c3cncs3)cc2)C(C)(C)C)cc1]

To a stirred solution of 2-({5-[4-(methoxycarbonyl)phenoxy]pentyl}oxy)acetic acid (200 mg), (2S,4R)-1-[(2S)-2-amino-3,3-dimethylbutanoyl]-4-hydroxy-N-{[4-(1,3-thiazol-5-yl)phenyl]methyl}pyrrolidine-2-carboxamide hydrogen chloride salt (149 mg, 0.32 mmol), N-ethyl-N-isopropylpropan-2-amine (185 mg, 1.44 mmol) in anhydrous N,N-dimethylformamide (5 mL) was added HATU (2-(7-aza-1H-benzotriazole-1-yl)-1,1,3,3-tetramethyluronium hexafluorophosphate) (203 mg, 0.54 mmol) at 0° C. The resulting mixture was allowed to warm up to rt and stirred at rt for 20 min. TLC and LC-MS showed formation of the desired product. The mixture was partitioned between ethyl acetate (100 mL) and water (50 mL). The organic layer was collected, washed with brine (50 mL), dried over anhydrous sodium sulfate, and concentrated under reduced pressure to give a crude residue which was purified by silica gel flash chromatography (eluent 2% methanol in methylene dichloride) to afford the titled product (yield 25%, 2 steps) as a white solid. Mass: ($ES^+$): m/z 695.30 [$M+H^+$].

Step 2: Synthesis of 4-{[5-({[(2S)-1-[(2S,4R)-4-hydroxy-2-({[4-(1,3-thiazol-5-yl)phenyl]methyl}carbamoyl)pyrrolidin-1-yl]-3,3-dimethyl-1-oxobutan-2-yl]carbamoyl}methoxy)pentyl]oxy}benzoic acid

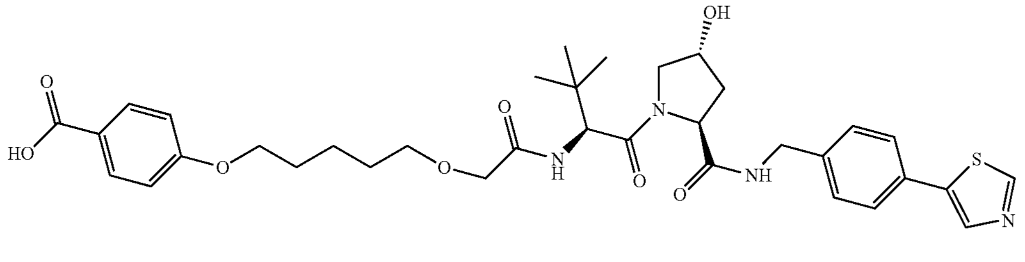 [SMILES: CC(C)(C)[C@H](NC(=O)COCCCCCOc1ccc(C(=O)O)cc1)C(=O)N1C[C@H](O)C[C@H]1C(=O)NCc1ccc(-c2cncs2)cc1]

To a stirred solution of methyl 4-{[5-({[(2S)-1-[(2S,4R)-4-hydroxy-2-({[4-(1,3-thiazol-5-yl)phenyl]methyl}carbamoyl)pyrrolidin-1-yl]-3,3-dimethyl-1-oxobutan-2-yl]carbamoyl}methoxy)pentyl]oxy}benzoate (150 mg, 0.22 mmol) in a mixed solvents of tetrahydrofuran (4 mL)-water (2 mL)-methanol (1 ml) was added lithium hydroxide monohydrate (36 mg, 0.86 mmol) at rt. The resulting mixture was stirred at 35° C. overnight. TLC and LC-MS showed formation of the desired product. The reaction mixture was acidified with aqueous HCl (3N) to pH=3-4 and extracted with methylene dichloride (50 mL×2). The organic layers were combined, washed with brine, dried over $Na_2SO_4$ and concentrated to afford the titled product (110 mg, crude) as a white solid which was used for next step without further purification. Mass: ($ES^+$): m/z 681.20 [$M+H^+$].

Step 3: Synthesis of Example E1

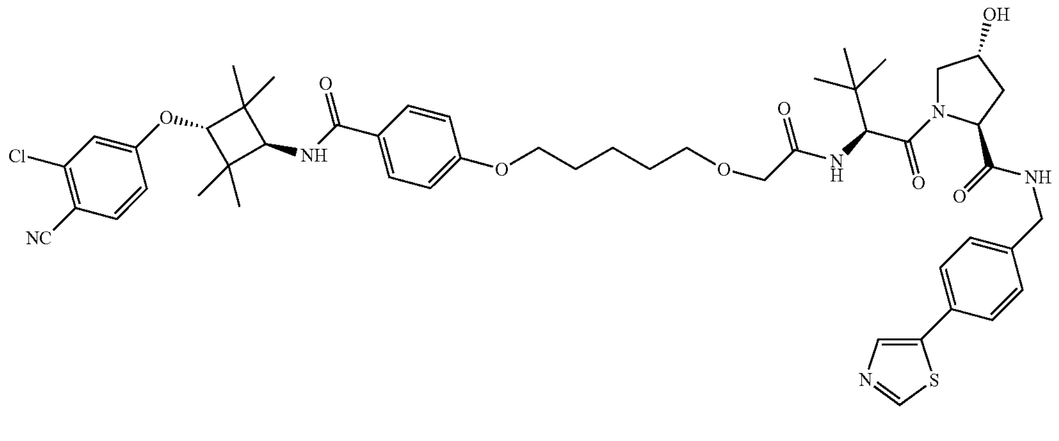 [SMILES: CC(C)(C)[C@H](NC(=O)COCCCCCOc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2cncs2)cc1]

To a stirred mixture of 4-{[5-({[(2S)-1-[(2S,4R)-4-hydroxy-2-({[4-(1,3-thiazol-5-yl)phenyl]methyl}carbamoyl) pyrrolidin-1-yl]-3,3-dimethyl-1-oxobutan-2-yl] carbamoyl}methoxy)pentyl]oxy}benzoic acid (110 mg, 0.16 mmol), 2-chloro-4-[trans-3-amino-2,2,4,4-tetramethylcyclobutoxy]benzonitrile hydrogen chloride salt (50 mg, 0.16 mmol), N-ethyl-N-isopropylpropan-2-amine (77 mg, 0.64 mmol) in anhydrous N,N-dimethylformamide (4 mL) was added HATU ((2-(7-Aza-1H-benzotriazole-1-yl)-1,1,3,3-tetramethyluronium hexafluorophosphate)) (68 mg, 0.18 mmol) at 0° C. The resulting mixture was allowed to warm up to rt and stirred at rt for 20 min. TLC and LC-MS showed formation of the desired product. The reaction mixture was partitioned between ethyl acetate (100 mL) and water (40 mL). The organic phase was separated, washed with brine (50 mL), dried over anhydrous sodium sulfate, and concentrated under reduced pressure to give a crude residue which was purified by preparative TLC (eluent: 5% methanol in methylene dichloride) to afford the titled product (yield 25%, 2 steps) as a white solid.

Synthesis of 2-({5-[4-(methoxycarbonyl)phenoxy] pentyl}oxy)acetic Acid

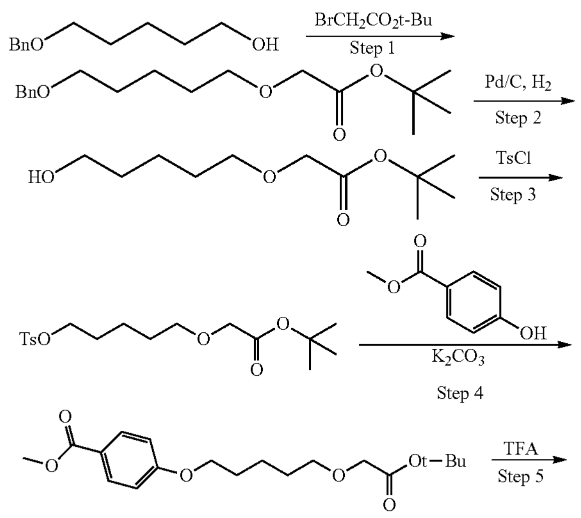

-continued

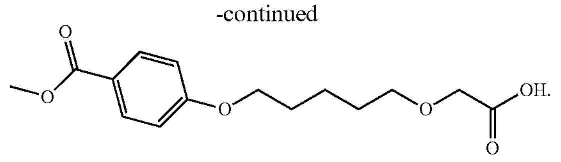

Step 1: Synthesis of tert-butyl 2-{[5-(benzyloxy) pentyl]oxy}acetate

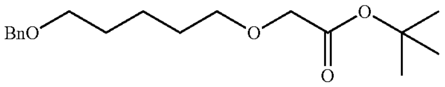 [SMILES: CC(C)(C)OC(=O)COCCCCCOCc1ccccc1]

To a stirred mixture of 5-(benzyloxy)pentan-1-ol (10 g, 51.5 mmol), tert-butyl 2-bromoacetate (40.2 g, 206 mmol) and tetrabutyl ammonium chloride (14.2 g, 51.5 mmol) in methylene dichloride (60 mL) was added sodium hydroxide (40 ml, 35% in water) at rt, and the resulting mixture was stirred at rt for 16 h. The reaction mixture was then partitioned between methylene dichloride (200 mL) and water (100 mL). The organic layer was collected and washed with brine (50 mL), dried over anhydrous sodium sulfate, and concentrated under reduced pressure to give a crude residue which was purified by silica gel flash chromatography (eluent: 5% ethyl acetate in hexane) to afford tert-butyl 2-{[5-(benzyloxy)pentyl]oxy}acetate (yield 31.6%) as light yellow oil. LC-MS: ($ES^+$): m/z 331.10 [$M+Na^+$], $^1H$ NMR (400 MHz, $CDCl_3$): δ 1.48 (s, 9H), 1.63-1.67 (m, 6H), 3.46-3.53 (m, 4H), 4.10 (s, 2H), 4.50 (s, 2H), 7.28-7.34 (m, 5H).

Step 2: Synthesis of tert-butyl 2-[(5-hydroxypentyl)oxy]acetate

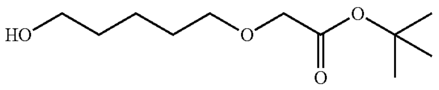

To a stirred solution of tert-butyl 2-{[5-(benzyloxy)pentyl]oxy}acetate (5 g, 16.2 mmol) in ethanol (100 ml) under a nitrogen atmosphere was added palladium on carbon (10%, 600 mg) at rt. The resulting mixture was stirred at 50° C. overnight under hydrogen atmosphere (hydrogen balloon). TLC showed formation of desired product. Palladium on carbon was removed through filtration and washed with ethyl acetate (50 mL). The filtrate was concentrated under reduced pressure to afford tert-butyl 2-[(5-hydroxypentyl)oxy]acetate (2.5 g, crude) as colorless oil which was used in next step without further purification.

Step 3: Synthesis of tert-butyl 2-({5-[(4-methylbenzenesulfonyl)oxy]pentyl}oxy)acetate

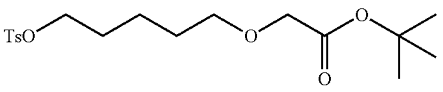 [SMILES: Cc1ccc(S(=O)(=O)OCCCCCOCC(=O)OC(C)(C)C)cc1]

To a stirred solution of tert-butyl 2-[(5-hydroxypentyl)oxy]acetate (2.5 g, crude) and triethylamine (3.5 g, 34.5 mmol) in anhydrous methylene dichloride (50 mL) was added a solution of 4-toluenesulfonyl chloride (2.7 g, 13.8 mmol) in anhydrous methylene dichloride (8 mL) drop wise at 0° C. The reaction mixture was allowed to warm up to rt and stirred at rt overnight. TLC showed formation of desired product. The mixture was quenched with aqueous solution of potassium carbonate (1N, 50 mL) at rt and extracted with ethyl acetate (50 mL×3). The organic layers were combined, washed with brine (50 mL), dried over anhydrous sodium sulfate, and concentrated under reduced pressure to give a crude residue which was purified by silica gel flash chromatography (eluent: 1% methanol in methylene dichloride) to afford tert-butyl 2-({5-[(4-methylbenzenesulfonyl)oxy]pentyl}oxy)acetate (yield 35.1%) as colorless oil. Mass: ($ES^+$): m/z 395.10 [$MNa^+$].

Step 4: Synthesis of Methyl 4-({5-[2-(tert-butoxy)-2-oxoethoxy]pentyl}oxy)benzoate

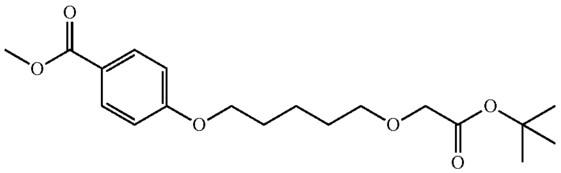 [SMILES: COC(=O)c1ccc(OCCCCCOCC(=O)OC(C)(C)C)cc1]

To a stirred mixture of tert-butyl 2-({5-[(4-methylbenzenesulfonyl)oxy]pentyl}oxy)acetate (1.0 g, 2.7 mmol) and potassium carbonate (266 mg, 1.6 mmol) in acetonitrile (15 mL) was added methyl 4-hydroxybenzoate (500 mg, 3.29 mmol) at rt. The resulting mixture was refluxed overnight. TLC showed formation of desired product. The reaction mixture was cooled to rt, and partitioned between ethyl acetate (150 mL) and water (50 mL). The organic layer was washed with washed with brine (50 mL), dried over anhydrous sodium sulfate, and concentrated under reduced pressure to give a crude residue which was purified by silica gel flash chromatography (eluent 10% ethyl acetate in hexane) to afford methyl 4-({5-[2-(tert-butoxy)-2-oxoethoxy]pentyl}oxy)benzoate (yield 33%) as colorless oil. Mass ($ES^+$): m/z 353.10 [$M+Na^+$]; $^1H$ NMR (400 MHz, $CDCl_3$): δ 1.48 (s, 9H), 1.55-1.61 (m, 2H), 1.68-1.72 (m, 2H), 1.80-1.87 (m, 2H), 3.55 (t, J=6.4 Hz, 2H), 3.88 (s, 3H), 3.96 (s, 2H), 4.02 (t, J=6.4 Hz, 2H), 6.89 (d, J=9.2 Hz, 2H), 7.97 (d, J=9.2 Hz, 2H).

Step 5: Synthesis of 2-({5-[4-(methoxycarbonyl)phenoxy]pentyl}oxy)acetic Acid

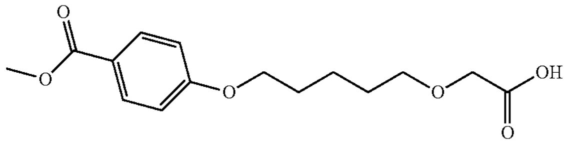 [SMILES: COC(=O)c1ccc(OCCCCCOCC(=O)O)cc1]

To a stirred solution of methyl 4-({5-[2-(tert-butoxy)-2-oxoethoxy]pentyl}oxy)benzoate (300 mg, 0.85 mmol) in DCM (4 mL) was added and TFA (2 ml) at rt, the resulting solution was stirred at room temperature for 1 h. TLC showed formation of the desired product. The solvent was evaporated to afford 2-({5-[4-(methoxycarbonyl)phenoxy]pentyl}oxy)acetic acid (200 mg, crude) as yellow oil which was used in next step without further purification.

Synthesis of an AR-Binding Warhead

WA: 2-chloro-4-(3-(4-hydroxyphenyl)-4,4-dimethyl-5-oxo-2-thioxoimidazolidin-1-yl)benzonitrile

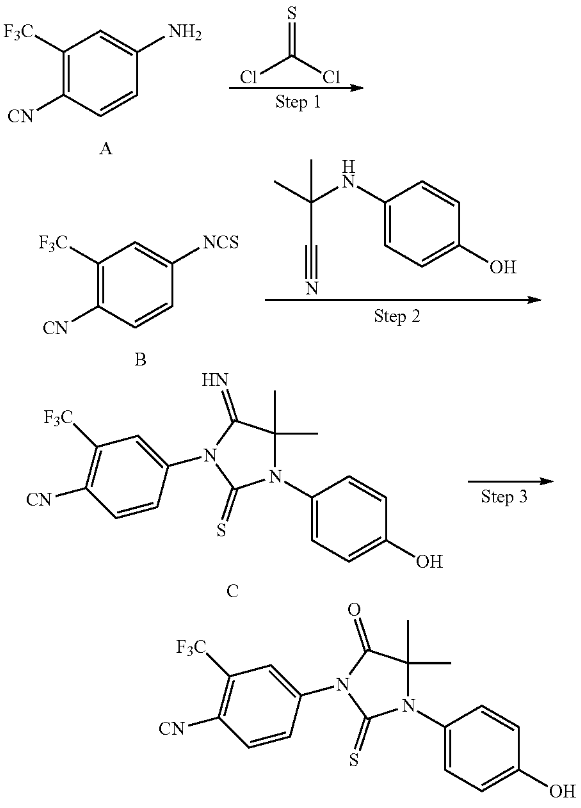

WA

Step 1: Synthesis of 2-trifluoromethyl-4-isothiocyanatobenzonitrile (B)

To a stirred solution of 4-amino-2-trifluomethylbenzonitrile (A, 1 g, 6.55 mmol) in dichloromethane (9 mL) was added sodium bicarbonate (2.21 g, 26.31 mmol) and water (9 mL). The resulting mixture was cooled to 0° C., to which thiophosgene (817 mg, 7.11 mmol) was added in drop wise in 30 min at 0° C. The resulting mixture was then warmed up to rt and stirred at rt for 1 h. The reaction mixture was diluted with dichloromethane (200 mL), washed with brine (50 mL×2), dried over anhydrous sodium sulfate and then concentrated under reduced pressure to give a crude residue. The residue was purified by flash silica gel chromatography (eluent: ethyl acetate/petroleum ether (v:v=1:30)) to give desired product (yield: 71%) $^1$HNMR (400 MHz, $CDCl_3$): δ 7.69 (d, J=8.0 Hz, 1H), 7.38 (s, 1H), 7.28 (m, 1H);

Step 2: Synthesis of 2-trifluoromethyl-4-[3-(4-hydroxyphenyl)-5-imino-4, 4-dimethyl-2-sulfanylideneimidazolidin-1-yl]benzonitrile (C)

To a stirred solution of 2-trifluoromethyl-4-isothiocyanatobenzonitrile (B, 399 mg, 2.05 mmol) in toluene (5 mL) was added 2-[(4-hydroxyphenyl)amino]-2-methylpropanenitrile (C, 300 mg, 1.70 mmol) and 4-dimethylaminopyridine (312 mg, 2.55 mmol). The resulting solution was then heated in an oil bath to 100° C. and stirred at the same temperature for 16h. LC-MS indicated formation of the desired product. The reaction mixture was concentrated under vacuum to give a crude reside which was purified by flash silica gel chromatography (eluent: ethyl acetate/petroleum ether (v:v=1:1)) to give desired product (yield: 48%) as a brown solid. LC-MS ($ES^+$): m/z 370.95 [$MH^+$], $t_R$=0.74 min (2.0 minute run);

Step 3: Synthesis of 2-trifluoromethyl-4-[3-(4-hydroxyphenyl)-4,4-dimethyl-5-oxo-2-sulfanylideneimidazolidin-1-yl]benzonitrile (WA)

To a stirred solution of 2-trifluomethyl-4-[3-(4-hydroxyphenyl)-5-imino-4, 4-dimethyl-2-sulfanylideneimidazolidin-1-yl]benzonitrile (C, 300 mg, 0.81 mmol) in methanol (6 mL) was added aqueous hydrogen chloride (2N, 3.0 mL). The resulting solution was then heated in an oil bath to 100° C. and stirred at the same temperature for 2h. The reaction mixture was diluted with water (30 mL), extracted with ethyl acetate (60 mL×3), washed with water (50 mL), dried over anhydrous sodium sulfate and concentrated under vacuum to give titled product (yield: 93%) as a yellow solid, which was used for the next step without any further purifications. LC-MS ($ES^+$): m/z 372.00 [$MH^+$], $t_R$=0.97 min (2.0 minute run).

Synthesis of VHL-Binding Warheads

ULM-1: (2S,4R)-1-((S)-2-amino-3,3-dimethylbutanoyl)-4-hydroxy-N-(4-(4-methylthiazol-5-yl)benzyl)pyrrolidine-2-carboxamide

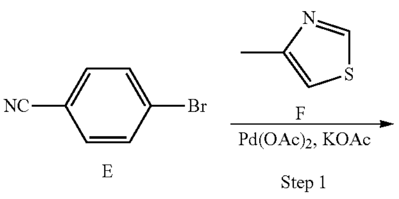

-continued

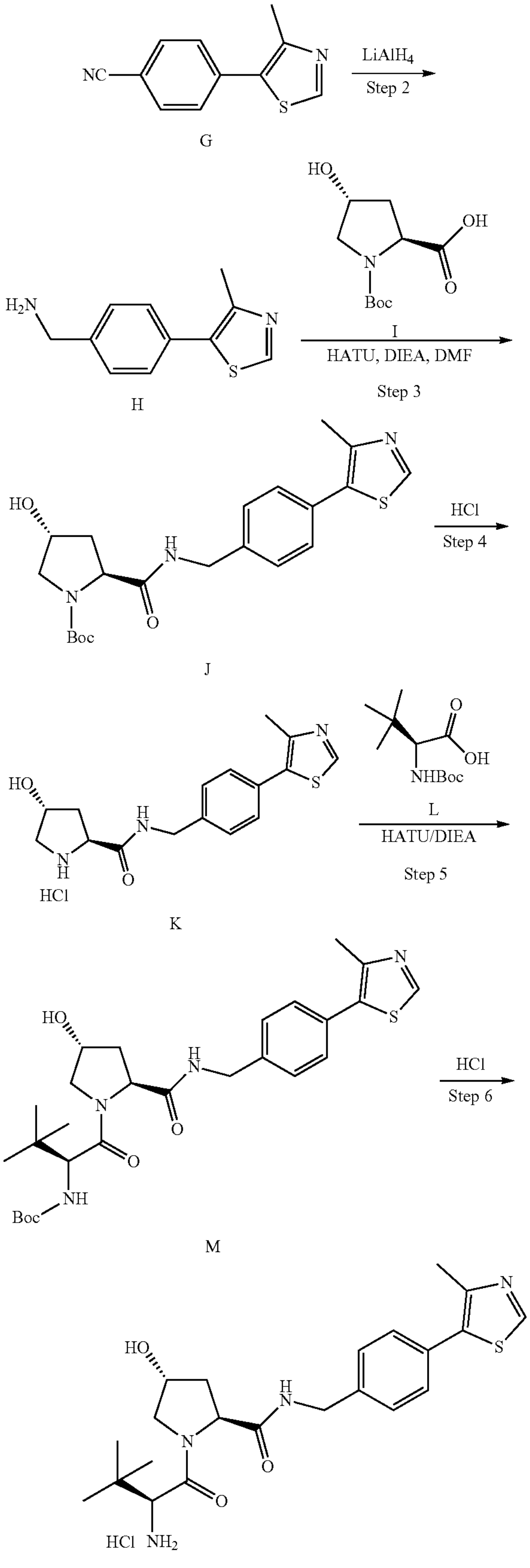

ULM-1

Step 1: Synthesis of 4-(4-methyl-1,3-thiazol-5-yl)benzonitrile (G)

To a stirred solution of 4-bromobenzonitrile (E, 20 g, 109.88 mmol) in DMA (250 mL) under a nitrogen atmosphere was added 4-methyl-1,3-thiazole (F, 21.88 g, 220.67 mmol), palladium (II) acetate (743 mg, 3.31 mmol) and potassium acetate (21.66 g, 220.71 mmol) at rt. The resulting solution was heated to 150° C. and stirred at this temperature for 5 h, LC-MS indicated formation of the desired product. The reaction was cooled to rt, diluted with 1 L of water and extracted with ethyl acetate (300 mL×3). The organic layers were combined, washed with saturated aqueous solution of sodium chloride (200 mL), dried over anhydrous sodium sulfate and then concentrated under reduced pressure to give a crude residue, which was purified by flash silica gel chromatography (eluent: ethyl acetate/petroleum ether, v:v=1:5) to give the G (yield: 91%) as a white solid.

Step 2: Synthesis of [4-(4-methyl-1,3-thiazol-5-yl) phenyl]methanamine (H)

To a stirred solution of 4-(4-methyl-1,3-thiazol-5-yl)benzonitrile (G, 35.0 g, 174.8 mmol) in tetrahydrofuran (1000 mL) was added $LiAlH_4$ (20.0 g, 526.3 mmol) in portions at 0° C. in 10 min under a nitrogen atmosphere. The resulting solution was then stirred at 60° C. for 3h. LC-MS indicated formation of the desired product. The reaction was then cooled to 0° C., quenched by the addition water (20 mL, added slowly), aq. solution of NaOH (15%, 20 mL) and water (60 mL). The resulting mixture was then extracted with ethyl acetate (300 mL×2). The organic layers were combined, washed with saturated aqueous solution of sodium chloride (100 mL), dried over anhydrous sodium sulfate and then concentrated under reduced pressure to give a crude residue, which was purified by flash silica gel chromatography (eluent: dichloromethane/methanol (v:v=10:1)) to give H (yield: 56%) as a yellow oil.

Step 3: Synthesis of tert-butyl (2S,4R)-4-hydroxy-2-({[4-(4-methyl-1,3-thiazol-5-yl)phenyl] methyl}carbamoyl)pyrrolidine-1-carboxylate (J)

To a stirred solution of (2S,4R)-1-[(tert-butoxy)carbonyl]-4-hydroxypyrrolidine-2-carboxylic acid (I, 2.7 g, 11.7 mmol) in N,N-dimethylformamide (20 mL) was added DIEA (2.52 g, 19.50 mmol), HATU (4.47 g, 11.76 mmol) and [4-(4-methyl-1,3-thiazol-5-yl)phenyl]methanamine (H, 2.0 g, 9.79 mmol) at rt. The resulting mixture was stirred at rt overnight, LC-MS indicated formation of the desired product. The reaction mixture was diluted with water (20 mL) and extracted with ethyl acetate (50 mL×3). The organic layers were combined, washed with saturated aqueous solution of sodium chloride (50 mL), dried over anhydrous sodium sulfate and then concentrated under reduced pressure to give a crude residue, which was purified by flash silica gel chromatography (eluent: dichloromethane/methanol (v:v=20:1)) to give J (yield: 56%) as a yellow solid.

Step 4: Synthesis of (2S,4R)-4-hydroxy-N-{[4-(4-methyl-1,3-thiazol-5-yl)phenyl]methyl}pyrrolidine-2-carboxamide hydrochloride (K)

To a stirred solution of tert-butyl (2S,4R)-4-hydroxy-2-({[4-(4-methyl-1,3-thiazol-5-yl)phenyl]methyl}carbamoyl) pyrrolidine-1-carboxylate (J, 45 g, 107.78 mmol), was added a solution of hydrogen chloride in dioxane (4N, 300 mL). The resulting solution was stirred at 20° C. for 2 h. The solids were collected by filtration to give K (yield: 98%) as a yellow solid, which was used for the next step without any further purification.

Step 5: Synthesis of tert-butyl N-[(2S)-1-[(2S,4R)-4-hydroxy-2-({[4-(4-methyl-1,3-thiazol-5-yl)phenyl] methyl}carbamoyl)pyrrolidin-1-yl]-3,3-dimethyl-1-oxobutan-2-yl]carbamate (M)

To a stirred solution of (2S)-2-{[(tert-butoxy)carbonyl] amino}-3,3-dimethylbutanoic acid (L, 15.7 g, 68.0 mmol) in N,N-dimethylformamide (500 mL) was added DIEA (29.2 g, 225.9 mmol), HATU (25.9 g, 68.1 mmol) and (2S,4R)-4-hydroxy-N-{[4-(4-methyl-1,3-thiazol-5-yl)phenyl] methyl} pyrrolidine-2-carboxamide hydrochloride (K, 20.0 g, 56.5 mmol) at rt. The resulting solution was stirred at rt for 16h, LC-MS indicated formation of the desired product. The reaction mixture was diluted by water (200 mL) and extracted with ethyl acetate (200 mL×3). The organic layers were combined, washed with saturated aqueous solution of sodium chloride (50 mL×2), dried over anhydrous sodium sulfate and then concentrated under reduced pressure to give a crude residue, which was purified by flash silica gel chromatography (eluent: ethyl acetate/petroleum ether (v:v=2:1)) to give M (yield: 51%) as a yellow solid.

Step 6: Synthesis of (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide hydrochloride (ULM-1)

To a stirred solution of tert-butyl N-[(2S)-1-[(2S,4R)-4-hydroxy-2-({[4-(4-methyl-1,3-thiazol-5-yl)phenyl] methyl}carbamoyl)pyrrolidin-1-yl]-3,3-dimethyl-1-oxobutan-2-yl]carbamate (M, 12 g, 22.61 mmol) in dioxane (20 mL) was added a solution of hydrogen chloride in dioxane (4N, 80 mL) at rt. The resulting solution was stirred at rt for 2 h, LC-MS indicated formation of the desired product. Precipitated solids were collected by filtration to give ULM-1 (yield: 48%) as a yellow solid. $^1$HNMR (400 MHz, $CD_3OD$): δ 9.84-9.82 (s, 1H), 7.58-7.54 (m, 4H), 4.71-4.41 (m, 4H), 4.13-4.08 (m, 1H), 3.86-3.71 (m, 2H), 3.36 (s, 1H), 2.60-2.58 (s, 3H), 2.35-2.07 (m, 2H), 1.19-1.12 (m, 9H). LC-MS ($ES^+$): m/z 431.11 [$MH^+$], $t_R$=0.73 min (2.0 minute run).

ULM-2: (2S,4R)-1-((S)-2-amino-3,3-dimethylbutanoyl)-4-hydroxy-N-(4-(thiazol-5-yl)benzyl)pyrrolidine-2-carboxamide

ULM-2

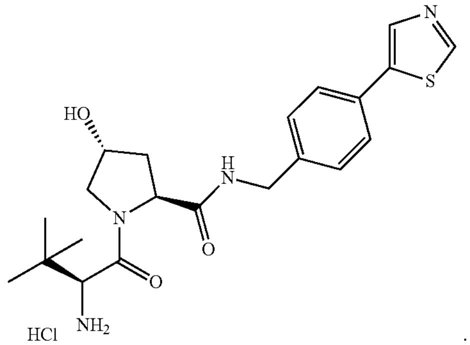

.

ULM-2 was synthesized according to similar procedure described above for the synthesis of ULM-1, utilizing 4-bromobenzonitrile and 1,3-thiazole as starting materials. LC-MS ($ES^+$): m/z 417.10 [$MH^+$], $t_R$=0.51 min (2.0 minute run).

ULM-3: (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide

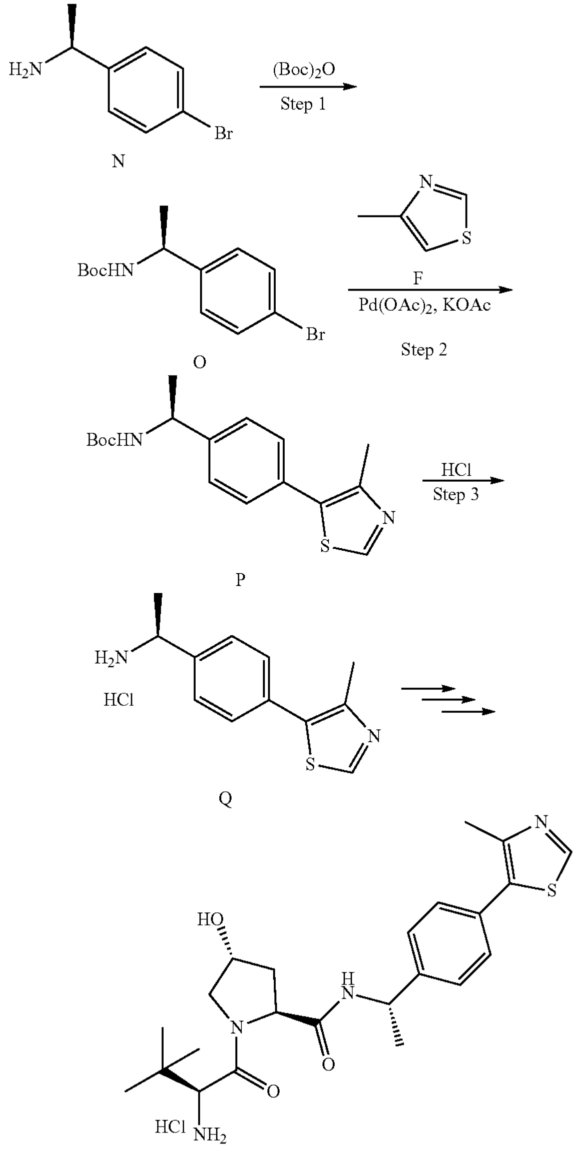

N

O

P

Q

ULM-3

Step 1: Synthesis of tert-butyl N-[(1S)-1-(4-bromophenyl)ethyl]carbamate (O)

To a stirred mixture of (1S)-1-(4-bromophenyl)ethan-1-amine (N, 10.0 g, 49.98 mmol) in dichloromethane (100 mL) was added $Et_3N$ (10.0 g, 99.01 mmol) and $(Boc)_2O$ (13.0 g, 59.63 mmol). The resulting mixture was stirred at rt for 2 h. The bulk of solvent was then removed under reduced pressure to give a crude residue, which was purified by flash silica gel chromatography (eluent: ethyl acetate/petroleum ether, v:v=1:10) to give O (yield: 99%) as a white solid.

Step 2: Synthesis of tert-butyl N-[(1S)-1-[4-(4-methyl-1,3-thiazol-5-yl)phenyl]ethyl]carbamate (P)

To a stirred solution of tert-butyl N-[(1S)-1-(4-bromophenyl)ethyl]carbamate (O, 15.0 g, 49.97 mmol) in DMA (100 mL), under an atmosphere of nitrogen, was added 4-methyl-1,3-thiazole (9.9 g, 99.84 mmol), potassium acetate (9.8 g, 99.86 mmol) and $Pd(OAc)_2$ (112.5 mg, 0.50 mmol) at rt. The resulting mixture was then stirred at 120° C. for 2h. The reaction mixture was then cooled to rt, diluted by water (120 mL), and extracted with ethyl acetate (200 mL×3). The organic layers were combined, dried over anhydrous sodium sulfate and then concentrated under reduced pressure to give a crude residue, which was purified by flash silica gel chromatography (eluent: ethyl acetate/petroleum ether, v:v=1:5) to give P (yield: 47%) as a white solid. LC-MS ($ES^+$): m/z 319.13 [$MH^+$], $t_R$=0.97 min (2.0 minute run).

Step 3. Synthesis of (1S)-1-[4-(4-methyl-1,3-thiazol-5-yl)phenyl]ethan-1-amine hydrochloride (Q)

To a stirred solution of tert-butyl N-[(1S)-1-[4-(4-methyl-1,3-thiazol-5-yl)phenyl]ethyl]carbamate (P, 7.5 g, 23.55 mmol) in methanol (20 mL) was bubbled in hydrogen chloride (gas) at rt for 2 h. Then the resulting mixture was concentrated under vacuum to give Q (yield: 86%) as a white solid, which was used in the next step without any further purifications.

Intermediate Q was converted to ULM-3 in a similar manner as described for the conversion of H to ULM-1. $^1H$ NMR (300 MHz, DMSO): δ 8.99 (s, 1H), 8.57-8.55 (d, J=7.8 Hz, 1H), 8.01 (br. s, 3H), 7.46-7.43 (d, J=8.4 Hz, 2H), 7.39-7.37 (d, J=8.4 Hz, 2H), 4.98-4.90 (m, 1H), 4.57-4.51 (m, 1H), 4.34 (br. s, 1H), 3.94-3.92 (m, 1H), 3.69-3.66 (m, 1H), 3.53-3.49 (m, 1H), 2.52 (s, 3H), 2.10-2.07 (m, 1H), 1.83-1.81 (m, 1H), 1.40-1.30 (m, 3H), 1.03 (s, 9H). LC-MS ($ES^+$): m/z 445.05 [$MH^+$], $t_R$=0.53 min (2.0 minute run).

Synthesis of Example E2

E2: (2S,4R)-1-((S)-2-(2-(3-(5-(4-(3-(4-cyano-3-(trifluoromethyl)phenyl)-5,5-dimethyl-4-oxo-2-thioxoimidazolidin-1-yl)phenoxy)pentyloxy)propoxy)acetamido)-3,3-dimethylbutanoyl)-4-hydroxy-N-(4-(4-methylthiazol-5-yl)benzyl)pyrrolidine-2-carboxamide

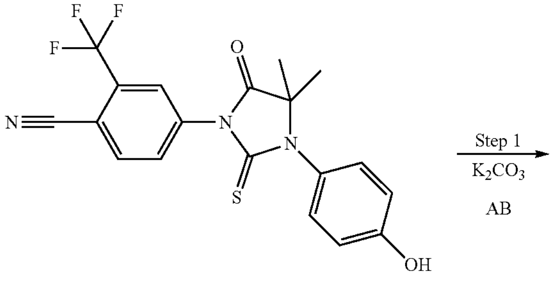

WA

-continued
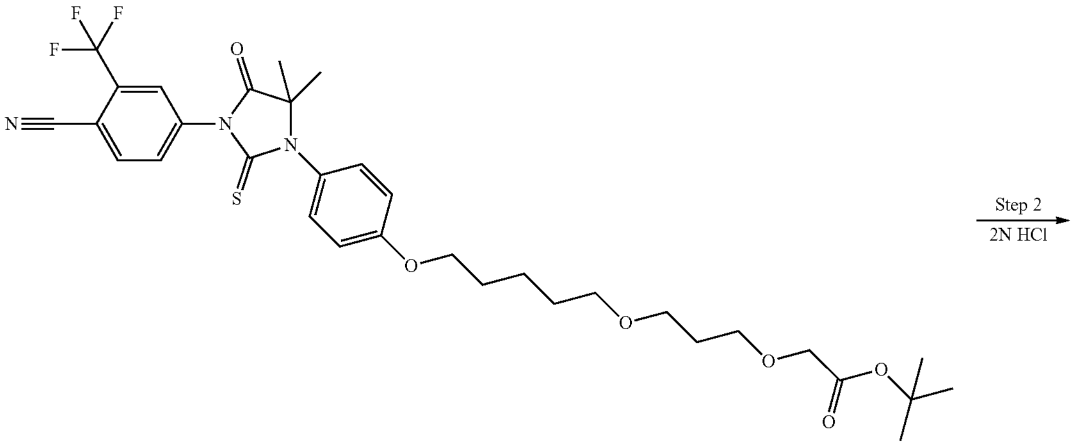
BG
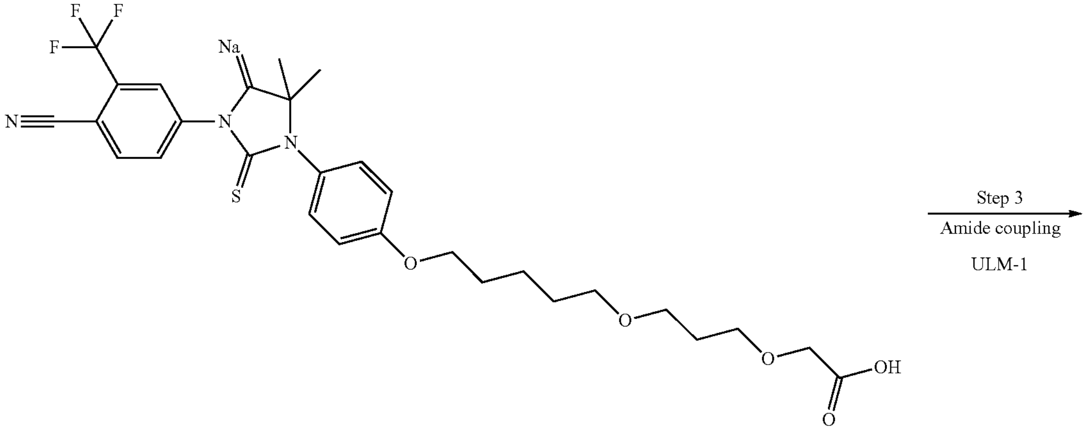
BH
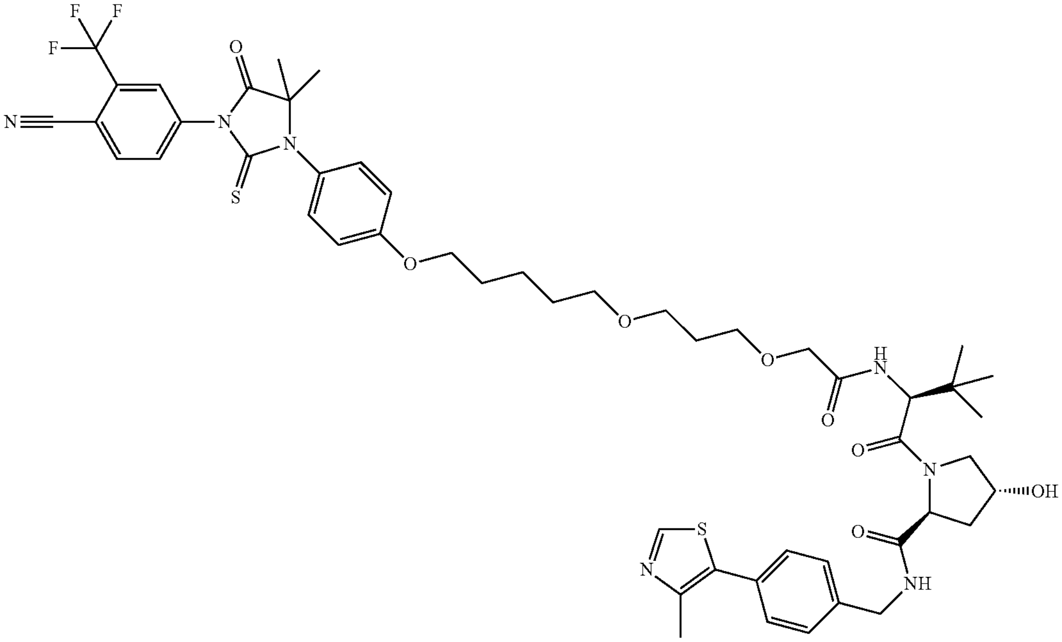
E2

Step 1: Synthesis of tert-butyl 2-(3-{[5-(4-{3-[4-cyano-3-(trifluoromethyl)phenyl]-5,5-dimethyl-4-oxo-2- sulfanylideneimidazolidin-1-yl}phenoxy) pentyl]oxy}propoxy)acetate (BG)

To a stirred solution of tert-butyl 2-[3-[(5-[[(4-methylbenzene)sulfonyl]oxy]pentyl)oxy]propoxy]acetate (AB, 150 mg, 0.35 mmol) in acetonitrile (10 mL) was added 4-[3-(4-hydroxyphenyl)-4,4-dimethyl-5-oxo-2-sulfanylideneimidazolidin-1-yl]-2-(trifluoromethyl)benzonitrile (ABM-3, 141 mg, 0.35 mmol) and potassium carbonate (144 mg, 1.04 mmol). The resulting mixture was stirred overnight at 80° C. in an oil bath. LC-MS indicated formation of the desired product. The reaction mixture was then extracted with ethyl acetate (20 mL×2). The organic layers were combined, washed with saturated aqueous solution of sodium chloride (20 mL), dried over anhydrous sodium sulfate and then concentrated under reduced pressure to give a crude residue, which was purified by flash silica gel chromatography (eluent: ethyl acetate/petroleum ether, v:v=1:1) to give 0.22 g of BG as a yellow oil. $^1$H NMR (400 MHz, $CDCl_3$): δ 7.96 (s, 2H), 7.86 (d, J=8.6 Hz, 1H), 7.19 (d, J=8.8 Hz, 2H), 7.02 (d, J=8.6 Hz, 2H), 4.50 (s, 2H), 4.30 (t, J=6.4 Hz, 2H), 4.02 (t, J=6.4 Hz, 2H), 3.53 (m, 2H), 3.44 (m, 2H), 1.96-1.80 (m, 4H), 1.69-1.53 (m, 2H), 1.49 (s, 6H), 1.48 (s, 9H), 1.44-1.22 (m, 2H); Mass ($ES^+$): m/z 686.35 [$MNa^+$].

Step 2: Synthesis of 2-(3-[[5-(4-[3-[4-cyano-3-(trifluoromethyl)phenyl]-5,5-dimethyl-4-oxo-2- sulfanylideneimidazolidin-1-yl]phenoxy)pentyl]oxy] propoxy)acetic acid (BH)

To a stirred solution of tert-butyl 2-(3-{[5-(4-{3-[4-cyano-3-(trifluoromethyl)phenyl]-5,5-dimethyl-4-oxo-2-sulfanylideneimidazolidin-1-yl}phenoxy)pentyl]oxy}propoxy)acetate (BG, 220 mg, 0.33 mmol) in dioxane (4.0 mL) was added hydrogen chloride (2N in water, 1.0 mL). The resulting mixture was stirred at 80° C. for 2h. LC-MS indicated formation of the desired product. The resulting mixture was concentrated under reduced pressure to provide 200 mg of BH as light yellow oil. Mass ($ES^+$): m/z 608.25 [$MH^+$].

Step 3: Synthesis of E2

To a stirred solution of 2-(3-[[5-(4-[3-[4-cyano-3-(trifluoromethyl)phenyl]-5,5-dimethyl-4-oxo-2-sulfanylideneimidazolidin-1-yl]phenoxy)pentyl]oxy]propoxy)acetic acid (BH, 160 mg, 0.26 mmol) in N,N-dimethylformamide (5 mL) was added (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide hydrochloride (ULM-1, 182 mg, 0.39 mmol), DIPEA (151 mg, 1.17 mmol), EDCI (101 mg, 0.53 mmol) and HOBt (70 mg, 0.52 mmol). The resulting mixture was stirred at rt for 5 h and LC-MS indicated formation of the desired product. Water (20 mL) was added to the reaction, the resulting mixture was extracted with ethyl acetate (20 mL×2). The organic layers were combined, washed with saturated aqueous solution of sodium chloride (20 mL), dried over anhydrous sodium sulfate and then concentrated under reduced pressure to give a crude residue. The residue was purified by Prep-HPLC to give 60 mg of Example 1 as a white solid. $^1$H NMR (400 MHz, $CD_3OD$): δ 8.88 (s, 1H), 8.16 (d, J=8.0 Hz, 2H), 8.00 (s, 1H), 7.49-7.42 (m, 4H), 7.28 (d, J=8.8 Hz, 2H), 7.06 (m, 2H), 4.87 (s, 1H), 4.59 (m, 3H), 4.37 (m, 1H), 4.05 (m, 4H), 3.88 (m, 2H), 3.65 (m, 2H), 3.58 (m, 2H), 3.50 (m, 2H), 2.48 (s, 3H), 2.25 (m, 1H), 2.10 (m, 1H), 1.90 (m, 2H), 1.80 (m, 2H), 1.66 (m, 2H), 1.56 (s, 8H), 1.04 (s, 9H); LC-MS ($ES^+$): m/z 1020.20 [$MH^+$±], $t_R$=2.28 min (3.6 minute run).

Androgen Receptor ELISA Assay

Compounds have been evaluated in this assay in LNCaP and/or VCaP cells utilizing similar protocols. The protocols used with VCaP cells are described below. The androgen receptor ELISA assay was performed using PathScan AR ELISA (Cell Signaling Catalog #12850) according to the following assay steps:

VCaP cells are seeded at 30,000 cells/well at a volume of 200 μL/well in VCaP assay medium [Phenol red free RPMI (Gibco Cat #11835-030); 5% Charcoal Stripped (Dextran treated) FBS (Omega Scientific, Cat #FB-04); Pen/Strep Life Technologies (Gibco Cat #: 10378-016); 0.1 nM R1881 (Sigma, Cat #R0908) is added upon the start of the assay, not during initial plating of the cells] in Corning 3904 plates. The cells are grown for a minimum of 3 days.

First, cells are dosed with compounds diluted in 0.1% DMSO—use a polypropylene plate according to the following protocol: (1)(i) make 1000× stock plate in DMSO; (ii) 20 mM stock diluted 1/6.7 with DMSO (5 μL+28.3 μL DMSO)=3 mM into row H; (iii) perform serial dilutions in ½ log doses (10 μL of compound+20 μL DMSO) from row H towards row B. Reserve row A for DMSO; (iv) 7 doses total (final concentration in this 1000× plate will be 3 mM, 1 mM, 333 μM, 111 μM, etc.). (2)(i) Make 10× stock plate in media; (ii) transfer 2.5 μL of the 1000× stock to a new 10× stock plate (use 12 channel pipet, start at A, DMSO control, work thru H). When 247.5 μL of media is added to this plate, it will serve as a 10× stock; (iii) make media+1 nM R1881 for making 10× stock plate; (iv) add 247.5 μL of media with 1 nM R1881 to each well of the 10× stock plate, mix.

Then 22 μL of 10× stock is added to cells and incubated for 24 h. 1× Cell Signaling Cell lysis buffer is made (Catalogue #9803; comes with the kit)—prepare for 50 μL/well. Keep on ice. Media is aspirated, and 50 μL 1× cell lysis buffer/well is added. The cells are placed on ice for 10 minutes. The solution is mixed and transferred to PCR plate, and centrifuged at 4 C for 10 minutes at 4000 rpm.

5 μL is transferred to fresh plate (use immediately or freeze −80 C); 115 μL ELISA Dilutant is added (0.15 ug/ml-0.075 ug/ml; comes with the PathScan ELISA).

Add 100 μL/well AR Elisa; cover and shake, 37 C for 2 hrs; dump, tap, wash 4×200 μL ELISA wash buffer; add 100 μL/well mouse AR detection Ab; cover and shake, 37 C for 1 hr; dump, tap, wash 4×200 μL ELISA wash buffer; add 100 μL/well anti-mouse—HRP conjugated Ab (comes with the kit); cover and shake, 37 C for 30 min; allow TMB reagent to come to RT; dump, tap, wash 4×200 μL Elisa wash buffer; tap; add 100 μL TMB, shake 5 min—while watching color. Add the stop reagent when light blue color develops. Add 100 μL Stop solution; shake and read at 450 nM.

Ligand Competition Assay

The experimental protocol is based on reference Gustafson et al. (*Angew. Chem. Int. Ed.*, 54: 9659-9662). HEK293 cells were transiently transfected using Fugene 6 to overexpress wildtype Androgen Receptor. During binding assay, transfected cells were grown in DMEM supplemented with 10% charcoal-stripped FBS. Cells were treated for two hours with the indicated competitor compound in the presence of 0.1 nM $^3$H-R1881. Cells were washed in PBS, lysed in 200 ul lysis buffer (2% SDS, 10% Glycerol, 10 mM Tris-HCl [pH 6.8]), and cleared with the addition of 300 ul of 10 mM Tris-HCl (pH 8.0). 300 ul of these lysates were added to 3 mL of Cytoscint (MP Biomedicals), and scintillation counting was performed on a Beckman LS 6000SC instrument. Counts (cpm) were normalized to total protein amount in each sample, as determined via the Pierce BCA Protein Assay Kit (Thermo Scientific) per the manufacturer's instructions.

Surface Plasmon Resonance (SPR) Method.

The SPR experiments were conducted on a Biacore3000 (GE Healthcare). His-tagged VHL protein was immobilized on a carboxymethylated dextran surface with nitriloacetic acid (NTA), taking advantage of NTA/$Ni^{2+}$ chelation. The prepared surface equilibrated over three hours in running buffer (10 mM HEPES buffer @ pH 7.4, 150 mM NaCl, 0.4 mg/mL BSA, 0.005% P20, 2% DMSO). All compounds were prepared in 100% DMSO stock plates with a top concentration of 500 mM in a 3× serial dilution. Compounds were transferred from the stock plate to the assay plate and diluted into running buffer (no DMSO) to measure direct binding. Equimolar concentration of ER-α was added to corresponding compound wells to measure cooperative binding. All compounds were run as a twelve point-concentration series with a final assay top concentration of 1 mM. Data analysis was performed in Scrubber 2 (BioLogic software, Campbell, Australia). Blanks were subtracted and data was corrected for DMSO against a standard DMSO curve. All reported $K_d$ values represent an average of at least N=2 and were obtained by fitting to a minimum of five concentrations using a 1:1 fitting algorithm.

AlphaLISA Assay Method for Measuring $K_d$ Values of a Trimeric Complex.

Compounds in 10% DMSO were serially diluted in 3-fold increments in an intermediate plate and then 3 uL was transferred to 384-well OptiPlates (Perkin Elmer, #6007290). Next, equimolar His-tagged VHL (made at Arvinas) and GST-tagged ER-α (Thermo Fisher, #A15677) were mixed to a final concentration of 14 nM each in Buffer A (50 mM HEPES, pH 7.5, 50 mM NaCl, 69 uM Brij, 0.1 mg/mL BSA) and then 13 uL of this mixture was transferred to each well of the 384-well assay plate containing compounds. After a ten-minute pre-incubation of the compound/protein mixture, 7.5 uL of anti-His conjugated AlphaLISA acceptor beads (PerkinElmer, #AL128M) diluted 100× in Buffer A was added to each well of the assay plate, followed by another 5 minute incubation in the dark. Finally, 7.5 uL of glutathione-conjugated AlphaLISA Donor beads (PerkinElmer, #6765301) diluted 100× in Buffer B was added, followed by another 5 minute incubation at room temperature in the dark. Assay plates were then read using a Synergy2 Multi-Mode plate reader (BioTek, Winooski, Vt.) after excitation thru a 680/30 nm excitation filter and collection of emission thru a 615/16 nm filter. A zero compound control was used to estimate 615 nm emission signal at 0% trimer formation, whereas, the max 615 nm emission value obtained at optimal compound concentration was used to estimate 100% trimer formation. Percent trimer formation was then calculated from 615 nm emission values using the following equation: ((615 nm observed−615 nm 0% control)/(615 nm 100% control−615 nm 0% control))*100%. All data points were then fit using a non-linear regression analysis in GraphPad Prism.

AlphaLISA Competitive Binding Assay for VHL.

Six microliters of 40 uM VHL-his stock (made at Arvinas) and 60 ul of 10 uM biotinylated VHL ligand probe (made at Arvinas) were added into 8 ml of Buffer A (50 mM HEPES, pH 7.5, 50 mM NaCl, 69 uM Brij, 0.1 mg/mL BSA). Final concentrations were 30 nM VHL and 75 nM probe and this mixture was incubated at room temperature for 10 minutes. Meanwhile, compounds in 10% DMSO were serially diluted in 3-fold increments in an intermediate plate and then 3 uL was transferred to 384-well OptiPlates (Perkin Elmer, #6007290). Next, 12 ul of the VHL-his/probe mix was added to each well of the assay plate and incubated 15 minutes at room temperature. After a ten-minute pre-incubation of the compound/protein mixture, 7.5 uL of anti-His conjugated AlphaLISA acceptor beads (Perkin Elmer, #AL128M) diluted 100× in Buffer A was added to each well of the assay plate, followed by another 5 minute incubation in the dark. Finally, 7.5 uL of streptavidin-conjugated AlphaLISA Donor beads (PerkinElmer, #6760002) diluted 100× in Buffer A was added followed by another 5 minutes incubation at room temperature in the dark. Assay plates were then read using a Synergy2 Multi-Mode plate reader (BioTek, Winooski, Vt.) after excitation thru a 680/30 nm excitation filter and collection of emission thru a 615/16 nm filter. A zero compound control was used to estimate 615 nm emission signal at 0% binding, whereas, signal after addition of 100× excess ligand (without biotin) was used to estimate 615 nm emission at 100% binding. Percent binding of compound was then calculated from 615 nm emission values using the following equation: (1−(615 nm compound−615 nm @ 100% binding)/(615 nm @ 0% binding−615 nm @ 100% binding))*100%. All data were then fit using a non-linear regression analysis in GraphPad Prism. Since the $K_d$ of the biotinylated VHL probe is 7.5 uM (data not shown), $K_d$ values were easily calculated from $IC_{50}$ values using the well-established Cheng-Prusoff equation.

Western Blot Analysis

Cultured cells were collected in lysis buffer containing 40 mM HEPES (pH 7.4), 140 mM NaCl, 2.5 mM EDTA, 1% NP-40, 0.1% SDS, and protease inhibitor cocktail. After 10 min of centrifugation (14,000 rpm), supernatant was collected for protein concentration determination by the bicinchoninic acid method and subjected for immunoblotting by standard protocol. Western blot results were visualized using Bio-Rad Clarity ECL Western Blotting Substrate on a Bio-Rad ChemiDoc MP imaging system.

c-Myc ELISA Assay Protocol

22RV-1 cells were purchased from ATCC and and cultured in RPMI+10% FBS media. Cells were harvested using trypsin (Gibco #25200-114), counted and seeded at 30,000 cells/well at a volume of 75 μL/well in RPMI+10% FBS media in 96-well plates. The cells were dosed with compounds diluted in 0.1% DMSO, incubated for 18h then washed and lysed in 50 uL RIPA buffer (50 mM Tris pH8, 150 mM NaCl, 1% Tx-100, 0.1% SDS, 0.5% sodium deoxycholate) supplemented with protease and phosphatase inhibitors. The lysates were clarified at 4000 rpm at 4° C. for 10 minutes then aliquots were added into a 96-well ELISA plate of Novex Human c-Myc ELISA kit from Life Technologies Catalog #KHO2041. 50 □L of c-Myc Detection antibody was added into every well, the plates incubated at room temperature for 3 hrs, then washed with ELISA wash buffer. 100 μL of the anti-rabbit IgG-HRP secondary antibody was added to each well and incubated at room temperature for 30 minutes. The plates were washed with ELISA wash buffer, 100 μL TMB added to each well, and then monitored every 5 minutes for a color change. 100 μL of stop solution is added and the plates read at 450 nm.

VHL Fluorescence Polarization (FP) Assay

VHL ligands were dissolved in DMSO (20 mM), and then serial diluted with 3-fold increments in DMSO. This serial dilution was diluted 10-fold with Assay Buffer (50 mM Tris pH 7.5, 200 mM NaCl, 2 mM DTT). Two μL of the 10% DMSO serial dilution series was pipetted into 384-well Corning 3575 plate. Purified VHL was diluted in Assay Buffer to 250 nM and 8 μL was transferred to each well. The plate was incubated for 1 hr. 5-FAM-DEALA[HYP]YIPMDDDFQLRSF peptide (synthesized by BIOMATIK) was diluted in Assay Buffer to 40 nM and 10 μL was pipetted to each well. The final concentration of the labeled peptide and VHL protein in the assay is 20 nM and 100 nM, respectively. The plate was incubated for 2 hrs, after which Fluorescence Polarization was determined with BioTek Cytation plate reader using the following BioTek filters: EX 485/20 EM 528/20. The percent inhibition was determined by normalizing to maximum and minimum polarization, and graphed against the log [ligand]. $IC_{50}$ values were determined using Prism 6.

In summary, the present disclosure provides a method and materials, including the theoretical understanding, to develop ligands that cause protein-protein interactions between targeted protein molecules. Accordingly, the present disclosure also defines the generic chemical structures for the compounds that have the ability to induce protein-protein interactions between any given targets.

While preferred embodiments of the disclosure have been shown and described herein, it will be understood that such embodiments are provided by way of example only. Numerous variations, changes and substitutions will occur to those skilled in the art without departing from the spirit of the disclosure. Accordingly, it is intended that the appended claims cover all such variations as fall within the spirit and scope of the disclosure.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A method of designing a bifunctional compound capable of effectuating protein-protein interactions via a ternary complex including a first protein (A) and a second protein (B) that is an E3 ubiquitin ligase, the method comprising:

(a) providing a plurality of bifunctional compounds of structure WA-Cn-WB, wherein WA is a warhead targeting the first protein A, WB is a warhead targeting the second protein B, and C is a connector with length or number of atoms n, covalently linked to WA and WB;

(b) determining a ternary binding potency of the plurality of bifunctional compounds, a binary binding potency of the plurality of bifunctional compounds with respect to the first protein A, and a binary binding potency of the plurality of bifunctional compounds with respect to the second protein B; and (c) selecting the bifunctional compound capable of effectuating protein-protein interactions from the plurality of bifunctional compounds that:

(i) has a ratio α that is greater than 1, wherein the ratio α is $IC_{50}^{A}$ over $IC_{50}^{A/B}$ or $IC_{50}^{B}$ over $IC_{50}^{B/A}$, or (ii) has a ratio $\alpha^{T}$ that is greater than 1, wherein the ratio $\alpha^{T}$ is a ratio of the lower of $IC_{50}^{A}$ and $IC_{50}^{B}$ over the half maximal ternary binding concentration ($IC_{50}^{T}$); and (d) administering an effective amount of the bifunctional compound capable of effectuating protein-protein interactions to a subject having a disease or disorder associated with the overexpression or activation of the protein A, wherein the bifunctional compound capable of effectuating protein-protein interactions effectuates degradation of the first protein A, and wherein the bifunctional compound capable of effectuating protein-protein interactions is effective at treating or ameliorating at least one symptom of the disease or disorder.

2. The method of claim 1, wherein at least one of: the warhead WA is a chemical group or moiety; the warhead WB is a chemical group or moiety; the connector C is a chemical group or moiety; and the warheads WA and WB are derived from compounds known to bind to proteins A and B, respectively.

3. The method of claim 1, wherein the connector C is a linear chain of carbon atoms or a linear chain of alternating carbon atoms and heteroatoms.

4. The method of claim 3, wherein any two heteroatoms in the connector C are separated by at least two carbon atoms.

5. The method of claim 1, wherein step (a) further comprises modifying the chain length or the number of atoms of the connector C to determine the appropriate chain length or the number of atoms of the connector C for the bifunctional compound capable of effectuating protein-protein interactions.

6. The method of claim 5, wherein determining the appropriate chain length or the number of atoms of the connector C for the bifunctional compound capable of effectuating protein-protein interactions comprises:

synthesizing the plurality of bifunctional compounds with the number of atoms in C varying n between 0 and 30 while keeping the warheads WA and WB constant.

7. The method of claim 6, wherein determining the appropriate chain length or the number of atoms of the connector C for the bifunctional compound capable of effectuating protein-protein interactions further comprises:

changing the attachment points on WA and WB that are used to link the warheads to the connector C.

8. The method of claims 1, wherein the connector C is a chain with branched groups and/or contains rings.

9. The method of claim 1, wherein step (b) further comprises:

determining the influence of the first protein or the second protein on a binding constant of another protein toward the plurality of bifunctional compounds to evaluate the capability of the plurality of bifunctional compounds to induce the protein-protein interaction.

10. The method of claim 9, wherein step (b) further comprises performing molecular dynamics simulations to demonstrate protein-protein interactions and other cross-domain interactions in ternary systems composed of the first protein A, the second protein B, and the plurality of bifunctional compounds to evaluate the capability of the plurality of bifunctional compounds to induce the protein-protein interaction.

11. The method of claim 10, wherein the first protein A and the second protein B are the same protein.

12. The method of claim 10, wherein the first protein A and the second protein B are different proteins.

13. The method of claim 1, wherein step (c) further comprises that the bifunctional compound capable of effectuating protein-protein interactions has a ternary complex that results in surface area burial greater than the sum of the surface area burial of the corresponding warhead monomers with the first and second proteins.

* * * * *